United States Patent
Tryggvason et al.

(10) Patent No.: US 10,240,124 B2
(45) Date of Patent: Mar. 26, 2019

(54) CELL CULTURE SUBSTRATE COMPRISING A LAMININ AND A CADHERIN

(71) Applicant: BioLamina AB, Solna (SE)

(72) Inventors: Karl Tryggvason, Djursholm (SE); Sergey Rodin, Stockholm (SE)

(73) Assignee: BioLamina AB, Solna (SE)

( * ) Notice: Subject to any disclaimer, the term of this patent is extended or adjusted under 35 U.S.C. 154(b) by 1174 days.

(21) Appl. No.: 14/360,040

(22) PCT Filed: Sep. 19, 2012

(86) PCT No.: PCT/IB2012/002214
§ 371 (c)(1),
(2) Date: May 22, 2014

(87) PCT Pub. No.: WO2013/041961
PCT Pub. Date: Mar. 28, 2013

(65) Prior Publication Data
US 2014/0315306 A1    Oct. 23, 2014

Related U.S. Application Data

(60) Provisional application No. 61/625,321, filed on Apr. 17, 2012, provisional application No. 61/624,588, (Continued)

(51) Int. Cl.
*C12N 5/074* (2010.01)
*C07K 14/705* (2006.01)
(Continued)

(52) U.S. Cl.
CPC .......... *C12N 5/0607* (2013.01); *C07K 14/705* (2013.01); *C07K 14/78* (2013.01);
(Continued)

(58) Field of Classification Search
None
See application file for complete search history.

(56) References Cited

U.S. PATENT DOCUMENTS 8,415,156 B2 * 4/2013 Tryggvason ........... C07K 14/78
424/93.7
2002/0076747 A1 * 6/2002 Price .................. A01K 67/0275
435/69.1
(Continued)

FOREIGN PATENT DOCUMENTS

JP      2006 087396 A    4/2006
WO   WO 2004/055155 A2  7/2004
(Continued)

OTHER PUBLICATIONS

Tenneille E Ludwig, Mark E Levenstein, Jeffrey M Jones, W Travis Berggren et al., Derivation of human embryonic stem cells in defined conditions, 2006, Nature Biotechnology, vol. 24, No. 2, pp. 185-187 with Supplemental Material.*
(Continued)

*Primary Examiner* — Renee Claytor
*Assistant Examiner* — Trent R Clarke
(74) *Attorney, Agent, or Firm* — Fay Sharpe LLP

(57) ABSTRACT

The present disclosure related to isolated laminin-521, methods for making recombinant laminin-521, host cells that express recombinant laminin-521, and compositions containing laminin-521. Laminin-521 can maintain stem cells in vitro pluripotency, enable self-renewal, and enable single cell survival of human embryonic stem cells. When pluripotent human embryonic stem cells are cultured on plates coated with recombinant laminin-521 (laminin-11), in the absence of differentiation inhibitors or feeder cells, the embryonic stem cells proliferate and maintain their pluripotency. It has also been discovered that human recombinant laminin-521 (laminin-11) provides single cell survival of
(Continued)

stem cells after complete dissociation into a single cell suspension. Useful cell culture mediums containing at most 3.9 ng/ml of beta fibroblast growth factor (bFGF) are also described herein.

10 Claims, 15 Drawing Sheets

Related U.S. Application Data filed on Apr. 16, 2012, provisional application No. 61/565,849, filed on Dec. 1, 2011, provisional application No. 61/565,380, filed on Nov. 30, 2011, provisional application No. 61/537,940, filed on Sep. 22, 2011.

(51) Int. Cl.
   C07K 14/78       (2006.01)
   C12M 1/12        (2006.01)
   C12N 5/00        (2006.01)
   C12N 5/0735      (2010.01)

(52) U.S. Cl.
   CPC ......... *C12M 25/00* (2013.01); *C12N 5/0068* (2013.01); *C12N 5/0606* (2013.01); *C12N 5/0696* (2013.01); *C12N 2501/115* (2013.01); *C12N 2533/52* (2013.01); *C12N 2533/90* (2013.01)

(56) References Cited

U.S. PATENT DOCUMENTS

| | | | |
|---|---|---|---|
| 2003/0044899 A1* | 3/2003 | Tryggvason | C07K 14/78 435/69.1 |
| 2008/0213885 A1 | 9/2008 | Tryggvason et al. | |
| 2010/0203635 A1 | 8/2010 | Tryggvason et al. | |
| 2010/0317916 A1 | 12/2010 | Scott, Jr. et al. | |
| 2011/0224233 A1* | 9/2011 | Xu | C07D 239/48 514/256 |
| 2012/0156254 A1 | 6/2012 | Tryggvason et al. | |
| 2012/0301962 A1* | 11/2012 | Thomson | C12N 5/0606 435/377 |

FOREIGN PATENT DOCUMENTS

| | | |
|---|---|---|
| WO | WO 2008/084401 A2 | 7/2008 |
| WO | WO2009006399 A1 | 1/2009 |
| WO | WO 2010/005995 A1 | 1/2010 |
| WO | WO2010137746 A1 | 12/2010 |

OTHER PUBLICATIONS

Tenneille E Ludwig, Veit Bergendahl, Mark E Levenstein, Junying Yu, Mitchell D Probasco & James A Thomson, Feeder-independent culture of human embryonic stem cells, 2006, Nature Methods, vol. 3, No. 8, pp. 637-646.*
Kaoru Kobayashi, Summary of recombinant human serum albumin development, 2006, Biologicals, vol. 34, pp. 55-59.*
Miyazaki et al., Recombinant human laminin isoforms can support the undifferentiated growth of human embryonic stem cells, 2008, Biochem. Biophys. Res. Commun., vol. 375, pp. 27-32.*
NPL pdf document "cc_surface area" downloaded from http://csmedia2.corning.com/LifeSciences/Media/pdf/cc_surface_areas.pdf on Jan. 24, 2015.*
Bettie et al., "Stem Cells Rapid Communication, Activin A Maintains Pluripotency of Human Embryonic Stem Cells in the Absence of Feeder Layers", Oct. 14, 2004, pp. 489-495, vol. 2, Alberto Hayek M.D., LaJolla, USA.
Chung et al.,"Human Embryonic Stem Cell Lines Generated without Embryo Destruction", *Cell Stem Cell* (2008), doi:10.1016/j.stem.2007.12.013.
Doi et al., Recombinant Human Laminin-10 ($\alpha 5\beta 1\gamma 1$), 2002, *The Journal of Biological Chemistry*, vol. 277, No. 15, pp. 12741-12748.
Levenstein et al., "Basic Fibroblast Growth Factor Support of Human Embryonic Stem Cell Self-Renewal", 2006, *Stem Cells*, vol. 24, pp. 568-574.
Mallon et al., "Review Toward Xeno-Free Culture of Human Embryonic Stem Cells", *The International Journal of Biochemistry & Cell Biology*, 38, Jan. 2006, pp. 1063-1075, NIH Stem Cell Unit, Bethesda, USA.
Nishiuchi et al., "Ligan-binding Specificities of Laminin-binding Integrins: A Comprehensive Survey of Laminin—Integrin Interactions Using Recombinant $\alpha 6\beta$ Integrins", 2006, *Matrix Biology*, vol. 25, pp. 189-197.
Pienado et al., "Transcriptional regulation of cadherins during development and carcinogenesis", *International Journal of Developmental Biology*, University of the Basque Country Pres, Leioa, Es., vol. 48, No. 5-6, Jan. 1, 2004.
Renwick et al., "Preimplantation genetic haplotyping: 127 diagnostic cycles demonstrating a robust, efficient alternative to direct mutation testing on single cells", *Reproductive Biomedicine Online*, Apr. 2010, vol. 20, No. 4, Apr. 2010.
Rodin et al., "Long-term self-renewal of human pluripotent stem cells on human recombinant lamin-511", *Nature Biotechnology*, Nature Publishing Group, New York, NY, vol. 28, No. 5, May 2010.
Suh et al., "Laminin regulates mouse embryonic stem cell migration: involvement of Epac1/Rap1 and Rap1/cdc42", *American Journal of Physiology—Cell Physiology*, vol. 28, No. 5, May 2010.
Taniguchi et al., "The C-Terminal Region of Laminin $\beta$ Chains Modulates the Integrin Binding Affinities of Laminins", *Journal of Biological Chemistry*, vol. 284, No. 12, 2009.
Unger et al., "Immortalized Human Skin Fibroblast Feeder Cells Support Growth and Maintenance of Both Human Embryonic and Induced Pluripotent Stem Cells", *Human Reproduction*, 2009, vol. 24, No. 10, pp. 2567-2581.
Wang et al., "Noggin and bFGF cooperate to maintain the pluripotency of human embryonic stem cells in the absence of feeder layers", 2005, *Biochemical and Biophysical Research Communication*, vol. 330, pp. 934-942.
Wang et al., "Inhibition of Capes-mediated Anika's is critical for Basic Fibroblast Growth Factor-sustained Culture of Human Pluripotent Stem Cells", *Biological Chemistry*, 2009, vol. 284, No. 49, pp. 34054-34064.
Xu et al., "Feeder-free growth of undifferentiated human embryonic stem cells", *Nature Biotechnology*, 2001, vol. 19.
Xu et al., "BMP4 Initiates Human Embryonic Stem Cell Differentiation to Trophoblastic", *Nature Biotechnology*, Dec. 2002, vol. 20, pp. 1261-1264.
International Search Report dated Feb. 27, 2013.
Ido, H. et al. "Molecular dissection of the—Dystroglycan- and Integrin-binding sites within the globular domain of human Laminin-10", J. Biol. Chem. 2004, pp. 10946-10954, vol. 279, JBC Papers in Press, USA.
Australian Office Action for Australian Application No. 2016213884, dated Oct. 11, 2017.
Singapore Search Report for Singapore Application No. 10201510405P, dated Sep. 13, 2017.
Rodin, S. et al., Nature Biotechnology, Jun. 2010, pp. 611-615, vol. 28, No. 6, Nature America, Inc., online.
Wang, G. et al., Biochemical and Biophysical Research Communications, Mar. 18, 2005, pp. 934-942, vol. 330, No. 3, Elsevier Inc., online.
Int J Biochem Cell Biol., Laminin-11, Aug. 31, 1999, (8):811-6.
GenBank, Laminin Subunit Alpha-5 Precursor [*Homo sapiens*]—Protein—NCBI, NP_005551.3, May 30, 2001.
GenBank, Laminin Beta 2 Chain [*Homo sapiens*]—Protein—NCBI, AAB34682.2, Jun. 2, 2000.

(56) References Cited

OTHER PUBLICATIONS

GenBank, Laminin Subunit Gamma 1 Precursor [*Homo sapiens*]—Protein—NCBI, NP_002284.3, May 24, 1999.

* cited by examiner

CELL CULTURE SUBSTRATE COMPRISING A LAMININ AND A CADHERIN

This application claims priority from U.S. Provisional Patent Application Ser. No. 61/537,940, filed Sep. 22, 2011; U.S. Provisional Patent Application Ser. No. 61/565,380, filed Nov. 30, 2011; U.S. Provisional Patent Application Ser. No. 61/565,849, filed Dec. 1, 2011; U.S. Provisional Patent Application Ser. No. 61/624,588, filed Apr. 16, 2012; and U.S. Provisional Patent Application Ser. No. 61/625,321, filed Apr. 17, 2012. The entireties of those provisional applications are fully incorporated by reference herein.

BACKGROUND

This application relates to cell biology, cell differentiation, cell therapy, molecular biology, proteins, recombinant human proteins, nucleic acids, and laminins.

Basal laminae (basement membranes) are sheet-like, cell-associated extracellular matrices that play a central role in cell growth, cellular differentiation, cell phenotype maintenance, tissue development, and tissue maintenance. They are present in virtually all tissues, and appear in the earliest stages of embryonic development.

Basal laminae are central to a variety of architectural and cell-interactive functions. For example:

1. They serve as architectural supports for tissues, providing adhesive substrata for cells.
2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.
3. Basal laminae create highly interactive surfaces that can promote cell migration and cell elongation during embryogenesis and wound repair. Following an injury, they provide a surface upon which cells regenerate to restore normal tissue function.
4. Basal laminae present information encoded in their structure to contacting cells that is important for cellular differentiation, prevention of apoptosis, and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. Additional components include proteoglycans such as agrin and perlecan and nidogens (entactins). To date, six type IV collagen polypeptide chains and at least twelve laminin subunit chains have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors on the one side, and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. The laminin molecule integrates various matrix and cell interactive functions into one molecule.

A laminin protein molecule comprises one α-chain subunit, one β-chain subunit, and one γ-chain subunit, all joined together in a trimer through a coiled-coil domain. FIG. 1 depicts the resulting structure of the laminin molecule. The twelve known laminin subunit chains can form at least 15 trimeric laminin types in native tissues. Within the trimeric laminin structures are identifiable domains that possess binding activity towards other laminin and basal lamina molecules, and membrane-bound receptors. FIG. 2 shows the three laminin chain subunits separately. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including laminin-521, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

There have been no reports of isolated laminin-521 that is free of other laminin chains. Thus far, there are no studies on the function of laminin-521. Attempts to purify laminin-521 from cell sources by affinity chromatography using laminin chain antibodies have been unsuccessful in eliminating, for example, laminin β1 chain, which is a component of laminin-411 and laminin-511. It would be desirable to provide compositions that contain laminin-521 (aka LN-521) and methods for making laminin-521.

Human embryonic stem (hES) cells hold promise for the development of regenerative medicine for a variety of diseases, such as spinal cord and cardiac injuries, type I diabetes and neurodegenerative disorders like Parkinson's disease. A stem cell is an undifferentiated cell from which specialized cells are subsequently derived. Embryonic stem cells possess extensive self-renewal capacity and pluripotency with the potential to differentiate into cells of all three germ layers. They are useful for therapeutic purposes and may provide unlimited sources of cells for tissue replacement therapies, drug screening, functional genomics and proteomics.

A prerequisite for the development of stem cell derived cells for regenerative medicine are methods that allow long-term cultures of pluripotent stem cells, chemically defined and repeatable differentiation protocols, as well as xeno-free cell culture systems. However, culturing of pluripotent human embryonic stem cells (hES cells) and induced pluripotent stem cells (hiPS cells) has encountered a number of problems. One major problem has been that hES cells grow slowly in clusters that need to be manually split for cell propagation. Dissociation of the cells usually leads to extensive cell death, the cloning efficiency of hES cells after complete dissociation being ≤1%.

Maintenance of pluripotent hES cells has required complex culture substrata, such as extracellular matrix protein mixtures like the mouse tumor derived Matrigel or fibroblast feeder cell layers, that may be immunogenic and toxic and that generate extensive batch to batch variability reducing reliability of the experiments. Thus far, the most successful feeder cell free substrate used for hES cell cultures is Matrigel, a complex tumor and BM-like extract obtained from murine Engelbreth-Holm-Swarm (EHS) sarcoma tumor tissues. Matrigel mainly contains murine LN-111, type IV collagen, perlecan and nidogen, but also varying amounts of other materials, including growth factors and cellular proteins and, therefore, its composition is undefined and varies from batch-to-batch. This variability can cause irreproducibility of scientific results, and due to the animal origin of the substratum makes Matrigel unacceptable for the expansion and maintenance of hES cells for human cell therapy.

However, successful development of more or less defined coating materials that support self-renewal of hES and hiPS cells has recently been reported. It has been reported that recombinant vitronectin supports adhesion and self-renewal of hES cells. An acrylate coating containing a variety of peptides from various ECM proteins has also been previously developed, and it has been shown that a synthetic methacrylate-based polymer also facilitated adhesion and self-renewal of hES cells.

One of the main problems with large-scale propagation of hES cells is that they poorly survive replating after dissociation into single cell suspension. This, in turn, makes passaging tedious and large-scale automated expansions impossible. However, hES cells released into single cell suspension using trypsin treatment in the presence of a rho-kinase (ROCK) inhibitor[10] or blebbistatin[11] can be plated and expanded from single clones, but the molecules are not components of the natural stem cell niche, and they affect the actin cytoskeleton and thus can cause cell damage. Therefore, the use of the ROCK inhibitor may not be a preferred solution for long-term expansion of hES cells aimed for cell therapy purposes.

For the purposes of regenerative medicine, there is a desire to develop methods that allow derivation and long-term cultures of pluripotent stem cells under chemically defined, xeno-free, pathogen-free, and stable batch-to-batch conditions. Moreover, such methods should allow fast and economically efficient scale-up to acquire large quantities of pluripotent hES/hiPS cells in a short period of time. Preferably, the methods should also allow clonal survival of human ES cells in media containing no synthetic inhibitor of apoptosis, that could facilitate scientific and clinical applications involving cell sorting or gene knock-out in the cells.

BRIEF DESCRIPTION

The present disclosure provides isolated laminin-521 (also known as LN-521 or laminin-11) and methods for producing isolated laminin-521. In further aspects, the present disclosure provides recombinant host cells that express laminin-521 chains and secrete recombinant laminin-521.

In other aspects, the present disclosure provides GMP quality laminin-521 for culturing cells for differentiation and maintenance for the purpose of developing cells for human cell therapy. The present disclosure also provides pharmaceutical compositions, comprising isolated laminin-521 together with a pharmaceutically acceptable carrier. Such pharmaceutical compositions can optionally be provided with other extracellular matrix components.

The present disclosure also provides methods to effectively generate amounts of isolated laminin-521 for various uses. In preferred embodiments of those uses, recombinant laminin-521 is used. Kits comprising an amount of isolated laminin-521, or pharmaceutical compositions thereof, effective for the desired effect, and instructions for the use thereof, are also disclosed.

The present disclosure also provides methods for culturing stem cells in monolayer cultures which facilitates cellular homogeneity, removal of the stem cells from a cell culture plate or other cellular support in single cell suspension, and replating stem cells in single cell suspension for passaging and expansion in significant dilutions that enable expansion of stem cell cultures and large scale production of such cells.

In further aspects, the present disclosure describes culturing pluripotent stem cells on laminin-521 in monolayer culture, removing stem cells from the cell culture plates along with other cell supporting materials in single cell suspension, and replating the stem cells from single cell suspension as single cells on a matrix containing laminin-521 such that this process can be performed in automated robotic systems with high efficiency.

In further aspects, the present disclosure provides improved medical devices and grafts, wherein the improvement comprises providing medical devices and grafts with an effective amount of isolated laminin-521.

In further aspects, the disclosure provides improved cell culture devices, and methods for preparing improved cell culture devices, for the growth and maintenance of phenotypes of cells in culture, by providing an effective amount of isolated laminin-521 to a cell culture device for cell attachment, and subsequent cell stasis, proliferation, differentiation, and/or migration.

In other aspect, the disclosure provides compositions, such as human recombinant laminin-521, and methods for culturing and rapid expanding of human embryonic stem cells in vitro in undifferentiated state. The methods comprise single cell dissociation of human embryonic stem cells and plating them on laminin-521 coated cell culture dishes in medium without any Rho-associated kinase (ROCK) inhibitor (e.g. without Y-27632) (Watanabe et al., *Nature Biotechnology* 25, 681-686 (2007)). The improvement provides a possibility to expand human embryonic stem cells in pluripotent state faster than in conventional human embryonic stem cell cultures.

In further aspects, the disclosure provides new materials, such as human recombinant laminin-521, which permit human embryonic cell survival after dissociation into single cell suspension. The improvement provides better cloning survival of human embryonic stem cells, which may be advantageous for isolating clones (e.g. after genetic manipulations) or obtaining homogeneous and uniformal human embryonic stem cell populations.

Disclosed in some embodiments is isolated recombinant laminin-521, comprising: an alpha chain comprising a polypeptide with at least 80% identity to a polypeptide sequence of SEQ ID NO: 1; a beta chain comprising a polypeptide with at least 70% identity to a polypeptide sequence of SEQ ID NO: 2; and a gamma chain comprising a polypeptide with at least 70% identity to a polypeptide sequence of SEQ ID NO: 3; wherein the alpha, beta, and gamma chains are assembled into recombinant laminin-521.

In further embodiments, the alpha chain polypeptide has at least 90% identity to the polypeptide sequence of SEQ ID NO: 1. The beta chain polypeptide may also have at least 90% identity to the polypeptide sequence of SEQ ID NO: 2. The gamma chain polypeptide may also have at least 90% identity to the polypeptide sequence of SEQ ID NO: 3.

In other embodiments, the alpha chain has the polypeptide sequence of SEQ ID NO: 1. Furthermore, the beta chain may have the polypeptide sequence of SEQ ID NO: 2. Even more specifically, the gamma chain may have the polypeptide sequence of SEQ ID NO: 3.

The beta chain polypeptide may have at least 80% identity to the polypeptide sequence of SEQ ID NO: 2. The gamma chain polypeptide may have at least 80% identity to the polypeptide sequence of SEQ ID NO: 3.

Also disclosed in embodiments is a pharmaceutical composition, comprising: a) the isolated recombinant laminin-521 of claim 1; and b) a pharmaceutically acceptable carrier.

Also disclosed in embodiments is a composition that enables self-renewal of pluripotent stem cells grown in vitro, comprising a growth medium and a coating thereover, the coating comprising recombinant laminin 521 (laminin-11).

The composition may further comprise a growth factor.

The composition may be devoid of any differentiation inhibitors. The composition may also be devoid of any feeder cells. The composition may also be devoid of any differentiation inductors. In some embodiments, the composition is devoid of any differentiation inhibitors, feeder cells, or differentiation inductors.

Also disclosed in embodiments is a method for maintaining the pluripotency of pluripotent stem cells in vitro, comprising: providing a substrate comprising a growth medium and a coating thereover, the coating comprising recombinant laminin 521 (laminin-11); dissociating pluripotent stem cells into a single cell suspension; and placing the pluripotent stem cells in the single cell suspension on the coating.

The growth medium may comprise a growth factor or growth factors. Exemplary growth factors include basic fibroblast growth factor and insulin growth factor.

Sometimes, the growth medium and the coating are devoid of any differentiation inhibitors. For example, leukemia inhibitor factor is not present.

The composition may be devoid of any feeder cells, such as mouse fibroblasts or human foreskin fibroblasts. The composition may be devoid of any differentiation inductors, such as Noggin or keratinocyte growth factor. In some embodiments, the composition is devoid of any differentiation inhibitors, feeder cells, or differentiation inductors.

The pluripotent stem cells may be placed on the laminin-521 coating as a monolayer.

The pluripotent stem cells may be placed on the coating at a density of 200 cells/mm$^2$ or less. Alternatively, the pluripotent stem cells may be placed on the coating at a density of 200 cells/mm$^2$ or more. The pluripotent stem cells can alternatively be placed on the coating such that no two stem cells contact each other.

Also disclosed in embodiments is isolated recombinant laminin-521 produced by a method comprising: providing host cells that express recombinant laminin-521, wherein the recombinant laminin-521 comprises: a first chain comprising a polypeptide with at least 80% identity to a polypeptide sequence of SEQ ID NO: 1, a second chain comprising a polypeptide with at least 70% identity to a polypeptide sequence of SEQ ID NO: 2, and a third chain comprising a polypeptide with at least 70% identity to a polypeptide sequence of SEQ ID NO: 3, wherein the first, second, and third chains are assembled into recombinant laminin-521; growing the host cells in a cell culture medium under conditions to stimulate expression of the recombinant laminin-521 chains; passing the host cell culture medium through a column, wherein the column contains a compound that binds to the recombinant laminin-521; washing the column to remove unbound materials; and eluting the bound recombinant laminin-521 from the column.

Described in other embodiments are methods of maintaining the pluripotency of pluripotent stem cells in vitro, comprising: receiving a substrate having a coating thereon, the coating containing an intact laminin; placing pluripotent stem cells and a cell culture medium on the substrate; and activating the PI3-kinase/Akt pathway.

The intact laminin may be laminin-521 or laminin-511. In some embodiments, the cell culture medium does not contain any growth factors, such as beta fibroblast growth factor (bFGF). The coating may also contain a cadherin. The pluripotent stem cells may be placed on the coating at a density of 200 cells/mm2 or less.

The present disclosure also relates to cell culture media that can be used to maintain stem cells in a pluripotent state. Described in various embodiments is a cell culture medium that provides nutrition to pluripotent stem cells, comprising from greater than zero to 3.9 ng/mL of basic fibroblast growth factor (bFGF).

The cell culture medium may comprise 3.5 ng/mL or less of bFGF, including from 0.5 to 3.5 ng/mL of bFGF.

The cell culture medium may further comprise at least one inorganic salt, at least one trace mineral, at least one energy substrate, at least one lipid, at least one amino acid, at least one vitamin, or at least one additional growth factor. In particular embodiments, the cell culture medium further comprises at least one inorganic salt, at least one trace mineral, at least one energy substrate, at least one lipid, at least one amino acid, and at least one vitamin.

The cell culture medium may not contain any one of (1) albumin, (2) insulin or an insulin substitute, or (3) transferrin or a transferrin substitute.

The cell culture medium may further comprise albumin, insulin, lithium chloride, GABA, TGF beta 1, pipecolic acid, L-glutamine, MEM non-essential amino acid solution, and DMEM/F12 solution.

The cell culture medium may further comprise at least one additional growth factor, at least one trace mineral, and at least one lipid.

Also disclosed is a system for maintaining pluripotent stem cells, comprising: a cell culture medium comprising from greater than zero to 3.9 ng/mL of basic fibroblast growth factor (bFGF); and a substrate for providing support to the stem cells.

The substrate may contain laminin-521 or laminin-511. The substrate may also contain a cadherin.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

In FIG. 4, the cells were cultured without ROCK inhibitor. In FIG. 5, the cells were cultured with ROCK inhibitor Y-27632.

DETAILED DESCRIPTION

Figure 1:
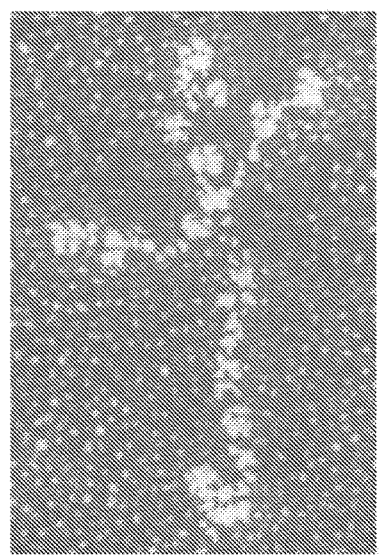
FIG. 1 is a rotary shadowing electron microscopy picture of a recombinant laminin molecule.
Figure 2:
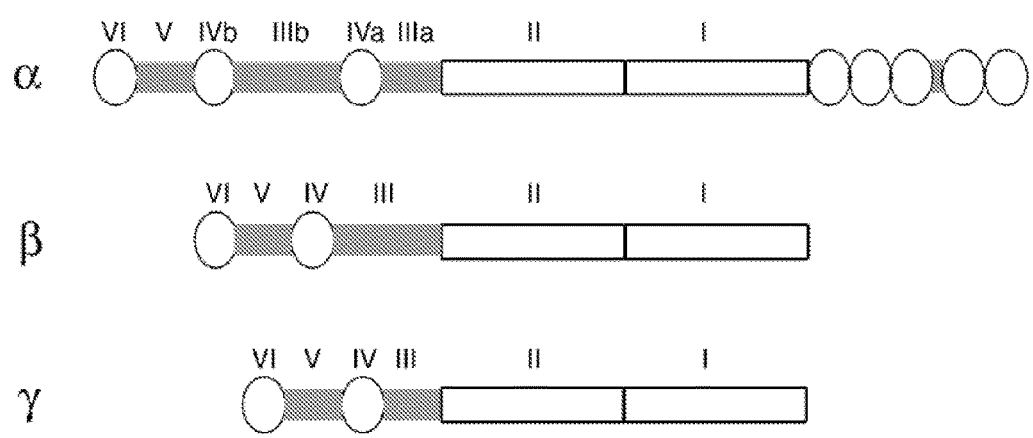
FIG. 2 shows the structural motifs of laminin α, β, and γ chains. The N-terminal, internal, and C-terminal globular domains are depicted as white ovals. The coiled-coil forming domains (I and II) are shown as white rectangles. The rod-like structures (domains V, IIIb, and IIIa) are depicted as grey rectangles.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

Unless otherwise stated, the techniques utilized in this application may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, Second Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), or the Ambion 1998 Catalog (Ambion, Austin, Tex.).

As used herein, the term "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). The "isolated" sequence may, however, be linked to other nucleotide sequences that do not naturally flank the recited sequence, such as a heterologous promoter sequence, or other vector sequences. It is not necessary for the isolated nucleic acid sequence to be free of other cellular material to be considered "isolated", as a nucleic acid sequence according to the disclosure may be part of an expression vector that is used to transfect host cells (see below).

The present disclosure provides recombinant expression vectors comprising a full length laminin β2 chain nucleic acid sequence (SEQ ID NO: 4) of the human laminin β2 chain. In some embodiments, the expression vectors comprise a nucleic acid encoded by SEQ ID NO: 4, operatively linked to a heterologous promoter (i.e. is not the naturally occurring promoter for the given β2 laminin chain). A promoter and a laminin β2 chain nucleic acid sequence are "operatively linked" when the promoter is capable of driving expression of the laminin β2 chain DNA into RNA.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors".

In the present disclosure, the expression of the laminin polypeptide sequence is directed by the promoter sequences of the disclosure, by operatively linking the promoter sequences of the disclosure to the gene to be expressed. In general, expression vectors of utility in recombinant DNA techniques are often in the form of plasmids. In the present specification, "plasmid" and "vector" may be used interchangeably, as the plasmid is the most commonly used form of vector. However, the disclosure is intended to include other forms of expression vectors, such as viral vectors (e.g., replication defective retroviruses, adenoviruses and adeno-associated viruses), which serve equivalent functions.

The vector may also contain additional sequences, such as a polylinker for subcloning of additional nucleic acid sequences, or a polyadenylation signal to effect proper polyadenylation of the transcript. The nature of the polyadenylation signal is not believed to be crucial to the successful practice of the methods of the disclosure, and any such sequence may be employed, including but not limited to the SV40 and bovine growth hormone poly-A sites. Also contemplated as an element of the vector is a termination sequence, which can serve to enhance message levels and to minimize readthrough from the construct into other sequences. Additionally, expression vectors typically have selectable markers, often in the form of antibiotic resistance genes, that permit selection of cells that carry these vectors.

In further embodiments, the present disclosure provides host cells transfected with the laminin β2 chain-expressing recombinant expression vectors disclosed herein. As used herein, the term "host cell" is intended to refer to a cell into which a nucleic acid of the present disclosure, such as a recombinant expression vector, has been introduced. Such cells may be prokaryotic, which can be used, for example, to rapidly produce a large amount of the expression vectors of the disclosure, or may be eukaryotic, for functional studies.

The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The host cells can be transiently or stably transfected with one or more of the expression vectors of the disclosure. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2.sup.nd Ed. (R. I. Freshney. 1987. Liss, Inc. New York, N.Y.).

In another aspect, the present disclosure provides an isolated full length human laminin β2 chain polypeptide consisting of the amino acid sequence of SEQ ID NO: 2.

As used herein, an "isolated polypeptide" refers to a polypeptide that is substantially free of other proteins, including other laminin chains, and gel agents, such as polyacrylamide and agarose. In preferred embodiments, the isolated laminin polypeptide is free of detectable contaminating laminin chains. Thus, the protein can either be isolated from natural sources, or recombinant protein can be isolated from the transfected host cells disclosed above.

In another aspect, the present disclosure provides isolated laminin-521. As used herein, the term "laminin-521" refers to the protein formed by joining α5, β2 and γ1 chains together. The term should be construed as encompassing both recombinant laminin-521 and heterotrimeric laminin-521 from naturally occurring sources. In preferred embodiments, the laminin-521 comprises recombinant laminin-521 (or "r-laminin-521").

As used herein, the term "r-laminin-521" refers to recombinant heterotrimeric laminin-521, expressed by a host cell that has been transfected with one or more expression vectors comprising at least one nucleic acid sequence encoding a laminin-521 chain selected from the α5, β2 and γ1 chains, or processed or secreted forms thereof. Such r-laminin-521 can thus comprise α5, β2, and γ1 sequences from a single organism, or from different organisms. Various laminin-521 chain DNA sequences are known in the art, and the use of any such sequence to prepare the r-laminin-521 of the disclosure is contemplated. (See, for example, Pouliot, N. et al., Experimental Cell Research 261(2):360-71, (2000); Kikkawa, Y. et al., Journal of Cell Science 113 (Pt 5):869-76, (2000); Church, H J. et al., Biochemical Journal 332 (Pt 2):491-8, (1998); Sorokin, L M. et al., Developmental Biology 189(2):285-300, (1997); Miner, J H. et al., Journal of Biological Chemistry 270(48):28523-6, (1995); Sorokin, L. et al., European Journal of Biochemistry 223(2):603-10, (1994)). In preferred embodiments, the r-laminin-521 is formed from recombinant human α5, β2, and γ1 polypeptide chains.

The disclosure encompasses those laminin molecules wherein only one or two chains that make up the recombinant heterotrimeric laminin-521 are encoded by endogenous laminin-521 chains. In preferred embodiments, each of the α5, β2, and γ1 polypeptide chains are expressed recombinantly.

The laminin-521 is an intact protein. The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

Laminin-521 is a secreted protein, which is capable of being directed to the endoplasmic reticulum (ER), secretory vesicles, and the extracellular space as a result of a signal sequence. If the secreted protein is released into the extracellular space, the secreted protein can undergo extracellular processing to produce a "mature" protein. Such processing events can be variable, and thus may yield different versions of the final "mature protein". For example, the lengths of the α5, β2, and γ1 chains may vary between proteins. However, the final mature protein still has the same functionality, even though the chain lengths vary. The isolated laminin-521 of the present disclosure includes heterotrimers comprising both the full length polypeptide chains and any such naturally processed laminin-521 polypeptide chains.

As used herein, a laminin-521 polypeptide chain refers to a polypeptide chain according to one or more of the following:

(a) a polypeptide chain that comprises a polypeptide structure selected from the group consisting of: R1-R2-R3, R1-R2-R4, R3, R4, R1-R3, R1-R4, R2-R3, and R2-R4, wherein R1 is an amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted laminin chain selected from the group consisting of a α5 chain, a β2 chain, and a γ1 chain; and R4 is a secreted α5, β2, or γ1 laminin chain that further comprises an epitope tag (such as those described below), which can be placed at any position within the laminin chain amino acid sequence; or (b) a polypeptide chain that is encoded by a polynucleotide that hybridizes under high or low stringency conditions to the coding regions, or portions thereof, of one or more of the recombinant laminin-521 chain DNA sequences disclosed herein (SEQ ID NO: 4, SEQ ID NO: 5, SEQ ID NO: 6), or complementary sequences thereof; or (c) a polypeptide chain that has at least 70% identity to one or more of the disclosed laminin-521 polypeptide chain amino acid sequences (SEQ ID NO: 1, SEQ ID NO: 2, SEQ ID NO: 3), preferably at least 80% identity, and most preferably at least about 90% identity.

"Stringency of hybridization" is used herein to refer to washing conditions under which nucleic acid hybrids are stable. The disclosure also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of ordinary skill in the art, the stability of hybrids is reflected in the melting temperature ($T_M$) of the hybrids. $T_M$ decreases approximately 1-1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. As used herein, high stringency refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

Also contemplated are laminin-521-encoding nucleic acid sequences that hybridize to the polynucleotides of the present disclosure at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altschul (Proc. Natl. Acad. Sci. USA 87:2264.2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score 100, wordlength=12, to determine nucleotide sequences identity to the nucleic acid molecules of the disclosure. BLAST protein searches are performed with the XBLAST program, score=50, wordlength=3, to determine an amino acid sequence identity to a polypeptide of the disclosure. To obtain gapped alignments for comparison purposes, Gapped BLAST is utilized as described in Altschul et al. (Nucleic Acids. Res. 25:3389-3402, 1997). When utilizing BLAST and Gapped BLAST programs, the default parameters of the respective programs (e.g., XBLAST and NBLAST) are used.

Further embodiments of the present disclosure include polynucleotides encoding laminin-521 chain polypeptides having at least 70% identity, preferably at least 80% identity, and most preferably at least 90% identity to one or more of the polypeptide sequences contained in SEQ ID NO: 4, SEQ ID NO: 5, and SEQ ID NO: 6.

As used herein, "α5 polynucleotide" refers to polynucleotides encoding a laminin α5 chain. Such polynucleotides can be characterized by one or more of the following: (a) polynucleotides that encode polypeptides which share at least 70% identity, preferably 80% identity, and most preferably at least 90% identity with a sequence selected of SEQ ID NO: 5; (b) polynucleotides that hybridize under low or high stringency conditions to the coding sequence of SEQ ID NO: 5 or complementary sequences thereof; or (c) polynucleotides encoding a laminin α5 chain polypeptide with a general structure selected from the group consisting of R1-R2-R3, R1-R2-R4, R3, R4, R1-R3, R1-R4, R2-R3, and R2-R4, wherein R1 and R2 are as described above, R3 is a secreted α5 chain, and R4 is a secreted α5 chain that comprises an epitope tag.

As used herein, "β2 polynucleotides" refers to polynucleotides encoding a β2 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 4; (b) polynucleotides that hybridize under low or high stringency conditions to the coding sequences of SEQ ID NO: 4, or complementary sequences thereof; or (c) polynucleotides encoding a polypeptide with a general structure selected from R1-R2-R3, R1-R2-R4, R3, R4, R1-R3, R1-R4, R2-R3, and R2-R4, wherein R1 and R2 are as described above, R3 is a secreted β2 chain, and R4 is a secreted β2 chain that comprises an epitope tag.

As used herein, "γ1 polynucleotides" refers to polynucleotides encoding a γ1 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 6; (b) polynucleotides that hybridize under low or high stringency conditions to the coding sequence of SEQ ID NO: 6 or complementary sequences thereof; or (c) polynucleotides that encode a polypeptide with a general structure selected from R1-R2-R3, R1-R2-R4, R3, R4, R1-R3, R1-R4, R2-R3, and R2-R4, wherein R1 and R2 are as described above, R3 is a secreted γ1 chain, and R4 is a secreted γ1 chain that comprises an epitope tag.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

In preferred embodiments, cDNAs encoding the laminin α5, β2 and γ1 chains, or fragments thereof, are subcloned into an expression vector. Alternatively, laminin α5, β2 and/or γ1 gene sequences, including one or more introns, can be used for sub-cloning into an expression vector.

In other aspects, the present disclosure provides laminin-521 expressing-cells that have been transfected with an expression vector containing promoter sequences that are operatively linked to nucleic acid sequences encoding at least one polypeptide sequence comprising a sequence selected from the group consisting of the α5, β2 and γ1 chains of laminin-521, wherein the transfected cells secrete heterotrimeric laminin-521 containing the recombinant laminin chain. In preferred embodiments, the cells are systematically transfected with recombinant expression vectors containing promoter sequences that are operatively linked to nucleic acid sequences encoding polypeptide sequences comprising the α5, β2 and γ1 chains of laminin-521, which are even more preferably all human chains. After the multiple transfections, the cells express recombinant laminin-521 chains, which form the heterotrimeric r-laminin-521.

Transfection of the expression vectors into eukaryotic cells can be accomplished via any technique known in the art, including but not limited to calcium phosphate co-precipitation, electroporation, or liposome mediated-, DEAE dextran mediated-, polycationic mediated-, or viral mediated transfection. Transfection of bacterial cells can be done by standard methods.

In preferred embodiments, the cells are stably transfected. Methods for stable transfection and selection of appropriate transfected cells are known in the art. In other preferred embodiments, a CMV promoter driven expression vector is used in a human kidney embryonic 293 cell line.

Any cell capable of expressing and secreting the r-laminin-521 can be used. Preferably, eukaryotic cells are used, and most preferably mammalian cells are used, including but not limited to kidney and epithelial cell lines. The promoter sequence used to drive expression of the individual chains or r-laminin-521 may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). Carbohydrate and disulfide post-translational modifications are believed to be required for laminin-521 protein folding and function. This makes the use of eukaryotic cells preferable for producing functional r-laminin-521, although other systems are useful for obtaining, for example, antigens for antibody production. In most preferred embodiments, the mammalian cells do not express the laminin β2 chain endogenously. In other preferred embodiments, the cells do not express all of the laminin-521 chains endogenously.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals.

In some embodiments, at least one of the laminin chain polypeptide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to any of the polypeptide chains comprising r-laminin-521, so long as the resulting r-laminin-521 remains functional.

In other embodiments, one of the r-laminin-521 chains is expressed as a fusion protein with a first epitope tag, and at least one other r-laminin chain is expressed as a fusion protein with a second different epitope tag. This permits multiple rounds of purification to be carried out. Alternatively, the same epitope tag can be used to create fusion proteins with more than one of the r-laminin chains.

In further embodiments, the epitope tag can be engineered to be cleavable from the r-laminin-521 chain(s). Alternatively, no epitope tag is fused to any of the r-laminin-521 chains, and the r-laminin-521 is isolated by standard techniques, including but not limited to affinity chromatography using laminin-521 specific antibodies or other laminin-521 binding molecules.

Media from cells transfected with a single laminin chain are initially analyzed on Western blots using laminin chain-specific antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for r-laminin-521 secretion and/or activity, by any appropriate method, including Western blot analysis and cell binding assays.

In preferred embodiments, purification of r-laminin-521 is accomplished by passing media from the transfected cells through an antibody affinity column. In some embodiments, antibodies against a peptide epitope expressed on at least one of the recombinant chains are attached to an affinity column, and bind the r-laminin-521 that has been secreted into the media. The r-laminin-521 is removed from the column by passing excess peptide over the column. Eluted fractions are analyzed by any appropriate method, including gel electrophoresis and Western blot analysis. In further embodiments, the peptide epitope can be cleaved after purification. In other embodiments, two or three separate r-laminin chains are expressed as fusion proteins, each with a different epitope tag, permitting two or three rounds of purification and a doubly or triply isolated r-laminin-521. The epitope tag can be engineered so as to be cleavable from the r-laminin-521 chain(s) after purification. Alternatively, no epitope tag is fused to any of the r-laminin-521 chains, and the r-laminin-521 is isolated by standard techniques, including but not limited to affinity chromatography using laminin-521 specific antibodies or other laminin-521 binding molecules.

In other embodiments, purification of r-laminin-521 is accomplished by passing media from the transfected cells through a gel-filtration chromatography column. Eluted fractions are analyzed by any appropriate method, including gel electrophoresis and Western blot analysis. Fractions containing r-laminin-521 are collected and purity of the specimen is evaluated by any appropriate method, including gel electrophoresis and Western blot analysis. In some embodiments, the protein solution can be passed through a gel-filtration chromatography column again to gain higher purity of the protein. In some embodiments, to achieve higher purity of r-laminin-521 solution, the media or r-laminin-521 solution from the previous purification steps can be passed through an ion-exchange column. Eluted fractions are analyzed by any appropriate method, including gel electrophoresis and Western blot analysis. Fractions containing r-laminin-521 are collected and purity of the specimen is evaluated by any appropriate method, including mentioned above.

The laminin-521 polypeptide chains of the present disclosure also include (i) substitutions with one or more of the non-conserved amino acid residues, where the substituted amino acid residues may or may not be one encoded by the genetic code, or (ii) substitution with one or more amino acid residues having substituent groups, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

In particular embodiments, the isolated laminin-521 comprises three chains. The first chain comprises a polypeptide with at least 80% identity to a polypeptide sequence of SEQ ID NO: 1 (i.e. the α5 laminin chain). The second chain comprises a polypeptide with at least 70% identity to a polypeptide sequence of SEQ ID NO: 2 (i.e. the β2 laminin chain). The third chain comprises a polypeptide with at least 70% identity to a polypeptide sequence of SEQ ID NO: 3 (i.e. the γ1 laminin chain). These first, second, and third chains are assembled into recombinant laminin-521.

In more specific embodiments, the polypeptide of the first chain has at least 80% identity to the polypeptide sequence of SEQ ID NO: 1, the polypeptide of the second chain has at least 80% identity to the polypeptide sequence of SEQ ID NO: 2, and the polypeptide of the third chain has at least 80% identity to the polypeptide sequence of SEQ ID NO: 3.

In more specific embodiments, the polypeptide of the first chain has at least 90% identity to the polypeptide sequence of SEQ ID NO: 1, the polypeptide of the second chain has at least 90% identity to the polypeptide sequence of SEQ ID NO: 2, and the polypeptide of the third chain has at least 90% identity to the polypeptide sequence of SEQ ID NO: 3.

In particular embodiments, the first chain comprises the polypeptide sequence of SEQ ID NO: 1, the second chain comprises the polypeptide sequence of SEQ ID NO: 2, and the third chain comprises the polypeptide sequence of SEQ ID NO: 3.

In particular embodiments, the first chain is the polypeptide sequence of SEQ ID NO: 1, the second chain is the polypeptide sequence of SEQ ID NO: 2, and the third chain is the polypeptide sequence of SEQ ID NO: 3.

The present disclosure further provides pharmaceutical compositions comprising isolated laminin-521 and a pharmaceutically acceptable carrier. In preferred embodiments, the pharmaceutical composition comprises isolated r-laminin-521. According to these aspects of the disclosure, other agents can be included in the pharmaceutical compositions, depending on the condition being treated. The pharmaceutical composition may further comprise one or more other compounds, including but not limited to any of the collagens, other laminin types, fibronectin, vitronectin, cadherins, integrins, α-dystroglycan, entactin/nidogen, α-dystroglycan, glycoproteins, proteoglycans, heparan sulfate proteoglycan, glycosaminoglycans, epidermal growth factor, vascular endothelial growth factor, fibroblast growth factor, or nerve growth factors, and peptide fragments thereof.

Pharmaceutical preparations comprising isolated laminin-521 can be prepared in any suitable form, and generally comprise the isolated laminin-521 in combination with a pharmaceutically acceptable carrier. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifingals, antioxidants, osmotic agents, and similar materials in composition and quantity as is conventional. Suitable solutions for use in accordance with the disclosure are sterile, are not harmful for the proposed application, and may be subjected to conventional pharmaceutical operations such as sterilization and/or may contain conventional adjuvants, such as preservatives, stabilizers, wetting agents, emulsifiers, buffers etc. For assistance in formulating the compositions of the present disclosure, one may refer to Remington's Pharmaceutical Sciences, 15th Ed., Mack Publishing Co., Easton, Pa. (1975).

In further aspects, the present disclosure comprises medical devices with improved biocompatibility, wherein the exterior surfaces of the devices are coated with isolated laminin-521 or pharmaceutical compositions thereof, alone or in combination with other proteins or agents that serve to increase the biocompatibility of the device surface. The coated device stimulates cell attachment (such as endothelial cell attachment), and provides for diminished inflammation and/or infection at the site of entry of the device.

Such medical devices can be of any material used for implantation into the body, and preferably are made of or coated with a biocompatible metal, such as stainless steel or titanium. Alternatively, the device is made of or coated with a ceramic material or a polymer, such as polyester, polyglycolic acid, or a polygalactose-polyglycolic acid copolymer.

If the device is made of a natural or synthetic biodegradable material in the form of a mesh, sheet or fabric, isolated laminin-521 or pharmaceutical compositions thereof may be applied directly to the surface thereof. Appropriate cells may then be cultured on the matrix to form transplantable or implantable devices, including dental abutment pieces, needles, metal pins or rods, indwelling catheters, colostomy tubes, surgical meshes and any other appliance for which coating with isolated laminin-521 is desirable. Alternatively, the devices may be implanted and cells may be permitted to attach in vivo.

Coupling of the isolated laminin-521 may be non-covalent (such as by adsorption), or by covalent means. The device may be immersed in, incubated in, or sprayed with the isolated laminin-521 or pharmaceutical compositions thereof.

The dosage regimen for various treatments using the isolated laminin-521 of the present disclosure is based on a variety of factors, including the type of injury or condition, the age, weight, sex, medical condition of the individual, the severity of the condition, and the route of administration. Thus, the dosage regimen may vary widely, but can be determined routinely by a physician using standard methods. Laminins are extremely potent molecules, and one or a few molecules per cell could produce an effect. Thus, effective doses in the pico-gram per milliliter range are possible if the delivery is optimized.

In other aspects, the present disclosure provides a new material, isolated laminin-521, which permits human embryonic stem cell survival after dissociation into single cell suspension. The stem cells were dissociated into single cell suspension by Trypsin-EDTA treatment, pelleted by centrifugation, resuspended into O3 medium, filtered through a 40 μm sieve, and plated at a density of 30 Kcells/cm$^2$ on cell culture dishes precoated by either isolated laminin-521, laminin-511, or Matrigel. After one day in culture, the cells plated on Matrigel died, as is known in the art. The human embryonic stem cells plated on laminin-521 and in most cases on laminin-511 survived and started to proliferate, forming small colonies of pluripotent cells.

In further aspects, the present disclosure provides a method to expand human embryonic stem cells in pluripotent state. It has been shown that human embryonic stem cells plated in single cell suspension on laminin-521 survived and proliferated at a higher rate than that of classical methods known in the art. After 3 passages (1 month) the cells passaged in a single cell suspension underwent the same number of cell divisions as that of cell cultures passaged in pieces on Matrigel after 20 passages (3 months). Therefore, the new method was advantageous in terms of time and labor, which may provide significant economical profits.

Laminin-521 is normally expressed and secreted by human pluripotent embryonic stem cells and can also be found in the kidneys, neuromuscular junctions, lungs, and placenta.

The availability of pure laminin-521 would enable studies of the effects of the protein on cellular differentiation and maintenance of cellular phenotypes. Thus, numerous research and therapeutic purposes including, but not limited to, treating injuries to tissues, promoting cell attachment, expansion and migration, ex vivo cell therapy, improving the biocompatibility of medical devices, and preparing improved cell culture devices and media, would be furthered if pure intact isolated laminin-521 were available. Also, the effects of pure laminin-521 on stem cells would be important to study as this protein is expressed in the early mammalian embryo.

Thus, there is a need in the art for isolated laminin-521 for research and therapeutic purposes, and methods for making isolated laminin-521. Laminin-521 can serve as a matrix for long-term self-renewal and fast multiplication of dissociated human ES and induced pluripotent stem (iPS) cells under completely chemically defined, feeder-free, and animal-protein-free (xeno-free) conditions. A LN-521 based system is easy to use and easy to automate, and allows fast scale-up of human ES/iPS cultures.

The present disclosure also relates to a cell culture medium that can be used to provide nutrition to cells, particularly stem cells. In this regard, stem cells typically require two things to be cultured: (1) a substrate or coating that provides a structural support for the stem cell; and (2) a cell culture medium to provide nutrition to the stem cell. The substrate or coating (1) is generally placed on, for example, a petri dish or some other container.

As used herein, the term "self-renewal" refers to the ability of the stem cell to go through numerous cycles of cell division and remain undifferentiated (i.e. pluripotent). Pluripotency itself refers to the ability of the stem cell to differentiate into any cell type. The term "proliferation" refers to the ability of the stem cell to divide. Survival refers to the ability of the stem cell to live, whether differentiated or undifferentiated, and does not require the stem cell to maintain its ability to divide or to differentiate.

The cell culture medium of the present disclosure is particularly suitable for being used with a substrate that contains laminin-521 and/or laminin-511. These laminins activate α6β1 integrins, which in turn leads to activation of the PI3K/Akt pathway. This increases the pluripotency, self-renewal, and/or proliferation of the stem cells. It is contemplated that the substrate may consist of laminin-521 or laminin-511, either intact, as separate chains, or as fragments thereof. Recombinant laminin-521 and recombinant laminin-511 are commercially available. Many different molecules can activate the PI3K/Akt pathway, though with different efficiencies. For example, TGF beta 1 and bFGF activate this pathway. The use of laminin-521 and/or laminin-511 allows the quantity of such molecules to be reduced in the cell culture medium. Laminin-521 conveys the highest dose of signal via α6β1 integrin, activating the PI3K/Akt pathway. The use of laminin-521 allows for single-cell suspension passaging without the addition of cell-detrimental rho-kinase (ROCK) inhibitor to increase cell survival after single-cell enzymatic dissociation. Previously, single-cell enzymatic passage of human ES cells without using artificial apoptosis inhibitors was impossible. The simplicity of the passaging procedure means the experimental variance is reduced and allows the process to be automated for high-throughput cell culture and results without the extensive training and costs of cell culture staff. In addition, human ES and iPS cells plated on laminin-521 or laminin-511 grow as a monolayer, which makes the culture homogeneous since cells are equally exposed to the matrix and the cell culture medium. Such human ES cell cultures, grown in a chemically defined, xeno-free environment on laminin-521, passaged as single cells in the absence of ROCK inhibitor expand continuously for months at an even better growth rate compared to cells grown on Matrigel passaged as clumps. These pluripotent long-term expanded cells homogeneously express Oct4 and remain karyotypically normal. Thus, one can obtain human ES and iPS cells with sustained survival and proliferation capacity.

The average contact area and spreading homogeneity is much larger for cells cultured on laminin-511 compared to other available substrata. Human ES cells grown on laminin-511 over 3 months maintain pluripotency and can generate teratomas after engraftment into SCID mice. Laminin-511 also supports the self-renewal of mouse ES cells for over 5 months without the presence of LIF or feeder cells, when other known matrices are unable to do so for longer than a couple of weeks.

The stem cells to be grown with this cell culture medium can be induced pluripotent stem cells, embryonic stem cells, adult stem cells, fetal stem cells, amniotic stem cells, and generally any pluripotent stem cell.

Typically, cell culture media include a large number and a large amount of various growth factors and cytokines to inhibit differentiation and improve proliferation. One advantage of the cell culture medium of the present disclosure is that it does not contain as many growth factors or cytokines, or such high amounts.

Most generally, the cell culture medium of the present disclosure requires lower amounts of basic fibroblast growth factor (bFGF) than typically used. It is contemplated that the cell culture medium may comprise from greater than zero to 3.9 nanograms per milliliter (ng/mL) of bFGF. The bFGF is human bFGF so that the cell culture medium is totally human and defined. In some more specific embodiments, the cell culture medium may comprise 3.5 or lower ng/mL of bFGF. In other embodiments, the cell culture medium may comprise from 0.5 to 3.5 ng/mL of bFGF. In some embodiments, the cell culture medium may have zero bFGF, i.e. no bFGF is present.

Generally, the cell culture medium includes a liquid phase in which at least one inorganic salt, at least one trace mineral, at least one energy substrate, at least one lipid, at least one amino acid, at least one vitamin, and at least one growth factor (besides bFGF) are dissolved. Table 1 below includes a list of various such ingredients which may be present in the cell culture medium of the present disclosure, and the minimum and maximum concentrations if the ingredient is present. The values are presented in scientific notation. For example, "4.1E-01" should be interpreted as $4.1 \times 10^{-01}$.

TABLE 1

| Ingredient | molar mass (g/mol) | Min. Conc. (mM) | Max. Conc. (mM) | Min. Conc. (ng/mL) | Max. Conc. (ng/mL) |
| --- | --- | --- | --- | --- | --- |
| INORGANIC SALTS | | | | | |
| Calcium chloride (Anhydrous) | 110.98 | 4.1E−01 | 1.6E+00 | 4.6E+04 | 1.8E+05 |
| HEPES | 238.3 | 5.9E+00 | 1.8E+01 | 1.4E+06 | 4.2E+06 |
| Lithium Chloride (LiCl) | 42.39 | 4.9E−01 | 1.5E+00 | 2.1E+04 | 6.2E+04 |
| Magnesium chloride (Anhydrous) | 95.21 | 1.2E−01 | 3.6E−01 | 1.1E+04 | 3.4E+04 |
| Magnesium Sulfate (MgSO$_4$) | 120.37 | 1.6E−01 | 4.8E−01 | 1.9E+04 | 5.8E+04 |
| Potassium chloride (KCl) | 74.55 | 1.6E+00 | 4.9E+00 | 1.2E+05 | 3.6E+05 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| Sodium bicarbonate ($NaHCO_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E−01 | 5.9E−01 | 2.8E+04 | 8.3E+04 |
| Sodium phosphate, monobasic monohydrate ($NaH_2PO_4$—$H_2O$) | 137.99 | 1.8E−01 | 5.3E−01 | 2.4E+04 | 7.3E+04 |
| TRACE MINERALS | | | | | |
| Ferric Nitrate ($Fe(NO_3)_3$—$9H_2O$) | 404 | 4.9E−05 | 1.9E−04 | 2.0E+01 | 7.5E+01 |
| Ferrous sulfate heptahydrate ($FeSO_4$—$7H_2O$) | 278.01 | 5.9E−04 | 1.8E−03 | 1.6E+02 | 4.9E+02 |
| Copper(II) sulfate pentahydrate ($CuSO_4$—$5H_2O$) | 249.69 | 2.0E−06 | 8.0E−06 | 5.1E−01 | 2.0E+00 |
| Zinc sulfate heptahydrate ($ZnSO_4$—$7H_2O$) | 287.56 | 5.9E−04 | 1.8E−03 | 1.7E+02 | 5.1E+02 |
| Ammonium Metavanadate $NH_4VO_3$ | 116.98 | 5.5E−06 | 1.6E−05 | 6.4E−01 | 1.9E+00 |
| Manganese Sulfate monohydrate ($MnSO_4$—$H_2O$) | 169.02 | 9.9E−07 | 3.0E−06 | 1.7E−01 | 5.0E−01 |
| $NiSO_4$—$6H_2O$ | 262.85 | 4.9E−07 | 1.5E−06 | 1.3E−01 | 3.8E−01 |
| Selenium | 78.96 | 8.9E−05 | 2.7E−04 | 7.0E+00 | 2.1E+01 |
| Sodium Meta Silicate $Na_2SiO_3$—$9H_2O$ | 284.2 | 4.8E−04 | 1.4E−03 | 1.4E+02 | 4.1E+02 |
| $SnCl_2$ | 189.62 | 6.2E−07 | 1.9E−06 | 1.2E−01 | 3.5E−01 |
| Molybdic Acid, Ammonium salt | 1235.86 | 9.9E−07 | 3.0E−06 | 1.2E+00 | 3.7E+00 |
| $CdCl_2$ | 183.32 | 6.1E−06 | 1.8E−05 | 1.1E+00 | 3.4E+00 |
| $CrCl_3$ | 158.36 | 9.9E−07 | 3.0E−06 | 1.6E−01 | 4.7E−01 |
| $AgNO_3$ | 169.87 | 4.9E−07 | 1.5E−06 | 8.3E−02 | 2.5E−01 |
| $AlCl_3$—$6H_2O$ | 241.43 | 2.4E−06 | 7.3E−06 | 5.9E−01 | 1.8E+00 |
| Barium Acetate ($Ba(C_2H_3O_2)_2$) | 255.42 | 4.9E−06 | 1.5E−05 | 1.3E+00 | 3.8E+00 |
| $CoCl_2$—$6H_2O$ | 237.93 | 4.9E−06 | 1.5E−05 | 1.2E+00 | 3.5E+00 |
| $GeO_2$ | 104.64 | 2.5E−06 | 7.5E−06 | 2.6E−01 | 7.8E−01 |
| KBr | 119 | 4.9E−07 | 1.5E−06 | 5.9E−02 | 1.8E−01 |
| KI | 166 | 5.0E−07 | 1.5E−06 | 8.3E−02 | 2.5E−01 |
| NaF | 41.99 | 4.9E−05 | 1.5E−04 | 2.1E+00 | 6.2E+00 |
| RbCl | 120.92 | 4.9E−06 | 1.5E−05 | 5.9E−01 | 1.8E+00 |
| $ZrOCl_2$—$8H_2O$ | 178.13 | 4.9E−06 | 1.5E−05 | 8.7E−01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E−01 | 5.9E−01 | 2.2E+04 | 6.5E+04 |
| LIPIDS | | | | | |
| Linoleic Acid | 280.45 | 9.4E−05 | 2.8E−04 | 2.6E+01 | 7.9E+01 |
| Lipoic Acid | 206.33 | 2.0E−04 | 7.8E−04 | 4.1E+01 | 1.6E+02 |
| Arachidonic Acid | 304.47 | 6.5E−06 | 1.9E−05 | 2.0E+00 | 5.9E+00 |
| Cholesterol | 386.65 | 5.6E−04 | 1.7E−03 | 2.2E+02 | 6.5E+02 |
| DL-alpha tocopherol-acetate | 472.74 | 1.5E−04 | 4.4E−04 | 6.9E+01 | 2.1E+02 |
| Linolenic Acid | 278.43 | 3.5E−05 | 1.0E−04 | 9.7E+00 | 2.9E+01 |
| Myristic Acid | 228.37 | 4.3E−05 | 1.3E−04 | 9.8E+00 | 2.9E+01 |
| Oleic Acid | 282.46 | 3.5E−05 | 1.0E−04 | 9.8E+00 | 2.9E+01 |
| Palmitic Acid | 256.42 | 3.8E−05 | 1.1E−04 | 9.8E+00 | 2.9E+01 |
| Palmitoleic acid | 254.408 | 3.9E−05 | 1.2E−04 | 9.8E+00 | 2.9E+01 |
| Stearic Acid | 284.48 | 3.4E−05 | 1.0E−04 | 9.8E+00 | 2.9E+01 |
| AMINO ACIDS | | | | | |
| L-Alanine | 89.09 | 2.5E−02 | 2.1E−01 | 2.2E+03 | 1.8E+04 |
| L-Arginine hydrochloride | 147.2 | 2.7E−01 | 1.5E+00 | 4.0E+04 | 2.2E+05 |
| L-Asparagine-$H_2O$ | 150.13 | 5.0E−02 | 2.1E−01 | 7.5E+03 | 3.1E+04 |
| L-Aspartic acid | 133.1 | 2.5E−02 | 2.1E−01 | 3.3E+03 | 2.7E+04 |
| L-Cysteine-HCl-$H_2O$ | 175.63 | 3.9E−02 | 1.2E−01 | 6.9E+03 | 2.1E+04 |
| L-Cystine dihydrochloride | 313.22 | 3.9E−02 | 1.2E−01 | 1.2E+04 | 3.7E+04 |
| L-Glutamic acid | 147.13 | 2.5E−02 | 2.1E−01 | 3.7E+03 | 3.0E+04 |
| L-Glutamine | 146.15 | 1.5E+00 | 4.4E+00 | 2.1E+05 | 6.4E+05 |
| Glycine | 75.07 | 1.5E−01 | 4.4E−01 | 1.1E+04 | 3.3E+04 |
| L-Histidine monohydrochloride monohydrate | 209.63 | 5.9E−02 | 1.8E−01 | 1.2E+04 | 3.7E+04 |
| L-Isoleucine | 131.17 | 1.6E−01 | 4.9E−01 | 2.1E+04 | 6.4E+04 |
| L-Leucine | 131.17 | 1.8E−01 | 5.3E−01 | 2.3E+04 | 7.0E+04 |
| L-Lysine hydrochloride | 182.65 | 2.0E−01 | 5.9E−01 | 3.6E+04 | 1.1E+05 |
| L-Methionine | 149.21 | 4.5E−02 | 1.4E−01 | 6.8E+03 | 2.0E+04 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| L-Phenylalanine | 165.19 | 8.5E−02 | 2.5E−01 | 1.4E+04 | 4.2E+04 |
| L-Proline | 115.13 | 1.1E−01 | 3.2E−01 | 1.2E+04 | 3.7E+04 |
| L-Serine | 105.09 | 1.5E−01 | 4.4E−01 | 1.5E+04 | 4.6E+04 |
| L-Threonine | 119.12 | 1.8E−01 | 5.3E−01 | 2.1E+04 | 6.3E+04 |
| L-Tryptophan | 204.23 | 1.7E−02 | 5.2E−02 | 3.5E+03 | 1.1E+04 |
| L-Tyrosine disodium salt hydrate | 225.15 | 8.4E−02 | 3.7E−01 | 1.9E+04 | 8.4E+04 |
| L-Valine | 117.15 | 1.8E−01 | 5.3E−01 | 2.1E+04 | 6.2E+04 |
| VITAMINS | | | | | |
| Ascorbic acid | 176.12 | 1.3E−01 | 3.8E−01 | 2.2E+04 | 6.7E+04 |
| Biotin | 244.31 | 5.6E−06 | 1.7E−05 | 1.4E+00 | 4.1E+00 |
| $B_{12}$ | 1355.37 | 2.0E−04 | 5.9E−04 | 2.7E+02 | 8.0E+02 |
| Choline chloride | 139.62 | 2.5E−02 | 7.5E−02 | 3.5E+03 | 1.1E+04 |
| D-Calcium pantothenate | 238.27 | 1.8E−03 | 1.4E−02 | 4.4E+02 | 3.4E+03 |
| Folic acid | 441.4 | 2.4E−03 | 7.1E−03 | 1.0E+03 | 3.1E+03 |
| i-Inositol | 180.16 | 2.7E−02 | 1.1E−01 | 4.9E+03 | 1.9E+04 |
| Niacinamide | 122.12 | 6.5E−03 | 2.0E−02 | 7.9E+02 | 2.4E+03 |
| Pyridoxine hydrochloride | 205.64 | 3.8E−03 | 1.1E−02 | 7.8E+02 | 2.4E+03 |
| Riboflavin | 376.36 | 2.3E−04 | 6.8E−04 | 8.6E+01 | 2.6E+02 |
| Thiamine hydrochloride | 337.27 | 3.3E−03 | 3.6E−02 | 1.1E+03 | 1.2E+04 |
| GROWTH FACTORS/PROTEINS | | | | | |
| GABA | 103.12 | 0 | 1.5E+00 | 0 | 1.5E+05 |
| Pipecolic Acid | 129 | 0 | 1.5E−03 | 0 | 1.9E+02 |
| bFGF | 18000 | 0 | 2.17E−07 | 0 | 3.9E+00 |
| TGF beta 1 | 25000 | 0 | 3.5E−08 | 0 | 8.8E−01 |
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferrin or a transferrin substitute.

In more specific embodiments, it is contemplated that the cell culture medium may not (1) contain albumin, (2) insulin or insulin substitute, (3) transferrin or transferrin substitute, or any combination of these three components.

It should be noted that other cell culture mediums may contain growth factors such as interleukin-1 beta (IL-1β or catabolin), interleukin-6 (IL6), or pigment epithelium derived factor (PEDF). Such growth factors are not present in the cell culture medium of the present disclosure.

One specific formula for a cell culture medium is provided in Table 2:

TABLE 2

| Ingredient | Amount | Unit |
|---|---|---|
| bFGF | 0.39 | microgram (μg) |
| Albumin | 1.34 | milligram (mg) |
| Insulin | 2 | mg |
| Lithium Chloride | 4.23 | mg |
| GABA | 0.01 | mg |
| TGF beta 1 | 0.06 | μg |
| Pipecolic acid | 0.013 | mg |
| L-glutamine | 2.92 | grams |
| MEM non-essential amino acid solution | 1 | mL |
| DMEM/F12 | 100 | mL |

In this regard, MEM non-essential amino acid solution is typically provided in a 100× concentrate. The MEM of Table 2 is used after dilution back to 1×, and contains the following amino acids in the following concentration listed in Table 3:

TABLE 3

| MEM Amino Acids | Concentration (ng/mL) |
|---|---|
| Glycine | 7.50E+03 |
| L-Alanine | 8.90E+03 |
| L-Asparagine | 1.32E+04 |
| L-Aspartic acid | 1.33E+04 |
| L-Proline | 1.15E+04 |
| L-Serine | 1.05E+04 |

DMEM/F12 contains the following ingredients listed in Table 4:

TABLE 4

| DMEM/F12 Ingredients | Concentration (ng/mL) |
| --- | --- |
| Glycine | 187.5 |
| L-Alanine | 44.5 |
| L-Arginine hydrochloride | 1475 |
| L-Asparagine-$H_2O$ | 75 |
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$—$5H_2O$) | 0.013 |
| Ferric Nitrate ($Fe(NO_3)_3$—$9H_2O$) | 0.5 |
| Ferric sulfate ($FeSO_4$—$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$—$H_2O$) | 625 |
| Zinc sulfate ($ZnSO_4$—$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |
| Putrescine 2HCl | 0.81 |
| Sodium Pyruvate | 550 |
| Thymidine | 3.65 |

The combination of the laminin substrate with the cell culture medium of the present disclosure results in a cell culture system that can be cheaper, yet provides higher efficiency in maintaining pluripotent stem cells. In essence, all that is required is a laminin and a minimal amount of nutrition. It is particularly contemplated that the laminin used in combination with this cell culture medium is either LN-511 or LN-521.

The following examples are for purposes of further illustrating the present disclosure. The examples are merely illustrative and are not intended to limit devices made in accordance with the disclosure to the materials, conditions, or process parameters set forth therein.

EXAMPLES

Example 1

Cloning of the Human Laminin 132 cDNA

The 5.6 kb fragment of human laminin β2 cDNA was PCR-amplified from human liver cDNA library (BD Biosciences) using primers 5'-GTGGTACCCACAGGCA-GAGTTGAC-3' (SEQ ID NO: 7) and 5'-GCTCTA-GAGCTCTTCAGTGCATAGGC-3' (SEQ ID NO: 8) thus introducing artificial XbaI and KpnI cutting sites on the ends of the fragment. To decrease the error rate during the PCR amplification, Phusion™ high-fidelity PCR Kit (Finnzymes) was used. Subsequently, the fragment was digested with XbaI and KpnI and subcloned into pSK vector digested with the same restriction endonucleases (pSKHLAMB2 plasmid). To verify the integrity of the sequence, several clones of pSKHLAMB2 plasmid were sequenced. Sequencing was performed on an ABI PRISM™ 310 Genetic Analyzer (Perkin Elmer) using ABI PRISM® BigDye™ Terminator Cycle Sequencing kit (PE Applied Biosystems). Only complete matches with the NCBI database human laminin β2 sequence were selected for further cloning.

Expression Constructs

For expression of the human laminin β2 chain pSKHLAMB2 plasmid was digested with XbaI and KpnI and subcloned into XbaI-KpnI treated pcDNA 3.1(+) vector (Invitrogen).

The constructs used for expression of human laminin α5 (HLN5Full.pcDNA construct) and γ1 (HG1 construct) have been described previously (Doi, M. et al., J. Biol. Chem. 277(15), 12741-8 (2002)).

Antibodies

Anti-laminin β2 (MAB2066) monoclonal antibody (mAb) was purchased from R@D Systems. Anti-laminin α5 mAb (2F7) was purchased from Abnova. Anti-laminin β1 mAb (MAB1921) was purchased from Chemicon. Anti-laminin γ1 (H-190) rabbit polyclonal antibody was purchased from Santa Cruz Biotechnology, Inc.

Production and Purification of Recombinant Laminin-521 r-laminin-521 was produced in human embryonic kidney cells (HEK293, ATCC CRL-1573) cultured in DMEM, 10% FCS in humidified 5% $CO_2$ atmosphere at 37° C. Wild-type cells were transfected using the standard calcium-phosphate method with the HG1 construct and stable colonies were selected using 100 mg/ml hygromycin (Cayla). All further cell culture and clonal expansion was carried out in continuous presence of relevant selection antibiotics. A highly expressing clone was then transfected with the human laminin β2 construct and stable clones were selected using 500 mg/ml G418 (Life Technologies). A clone highly expressing both laminin γ1 and laminin β2 was finally transfected with the HLN5Full.pcDNA construct and stable colonies were selected using 200 mg/ml zeocin (Cayla). The clones showing the highest secretion were expanded further.

For production of r-laminin-521, confluent cells were cultured in DMEM for up to five days. r-laminin-521 was affinity purified using anti-FLAG M2 matrix (Sigma). The collected medium was incubated in batch mode with the matrix overnight at 4° C. with agitation. Bound r-laminin-521 was competitively eluted with 50 mg/ml FLAG peptide (Sigma) in TBS/E (50 mM Tris-Cl, pH 7.5, 150 mM NaCl, 1 mM EDTA) at room temperature. The elute was concentrated and the buffer was replaced by PBS using 30 kD cut-off ultrafiltration (Millipore). Finally the concentrated solution was passed through 0.2 mm filter to remove self-aggregated polymers.

Characterization of Recombinant Laminin-521

Figure 3:
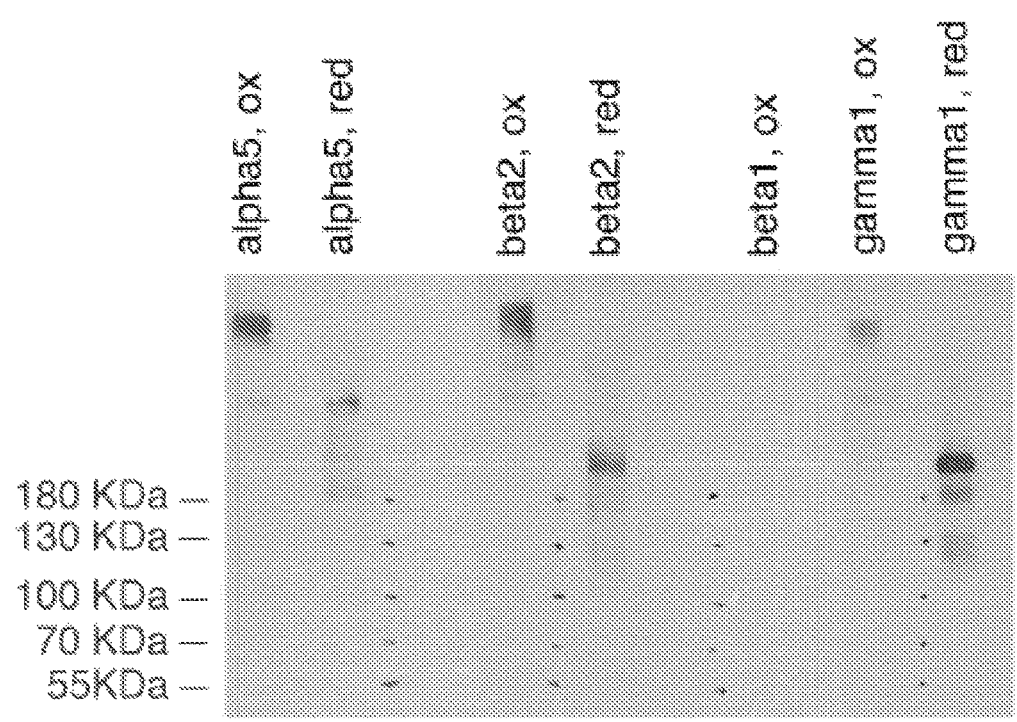
FIG. 3 shows the results of characterization of human recombinant laminin-521 using SDS-PAGE. An immunoblot of recombinant laminin-521 was made under non-reducing (labeled as ox) and reducing (labeled as red) conditions. Proteins on 3-8% gels were transferred onto PVDF membranes followed by staining with antibodies to laminin α5 (2F7), β2 (MAB2066), β1 (MAB1921) and γ1 (H-19).

Secreted laminin in medium and after purification was characterized using 3-8% gradient SDS-PAGE. Proteins were visualized using Sypro staining (Bio-Rad) or transferred onto PVDF (FIG. 3). The membranes were probed with antibodies described above. After washing, the membranes were incubated with HRP-conjugated goat antibodies. The immunoreactivity was detected by a chemiluminescent kit (Life Science Products) according to the manufacturer's instructions.

Methods

Human ES Cell Cultures.

Human ES cells were cultured on r-laminin-521-coated laboratory dishes in chemically defined O3 medium (described in Rodin et al., Nature Biotechnol., vol. 28, pp. 611-615 (2010)) at 37° C. in 5% CO2. Cells were routinely passed once every 10-12 days by exposure to Trypsin-EDTA solution (GIBCO Invitrogen) for 5 minutes at 37° C. They were then gently pipetted to break into single-cell suspension and defined trypsin inhibitor (GIBCO Invitrogen) was added. The cell suspension was centrifuged at for 4 minutes, the supernatant discarded, the cell pellet resuspended in prewarmed O3 medium, and cells were then passed through a 40 μm sieve. After that cells were plated on new r-laminin-521-coated dishes at a concentration 30 Kcells/cm$^2$ (1:25-1:30 split ratio). Cells were fed once a day with fresh medium prewarmed in an incubator for 1 hour, except for the first day after a passage, when only a few drops of fresh medium were added. Control cells of the same line were cultured on Matrigel (BD Biosciences) in O3 medium as described in Rodin et al., Nature Biotechnol., vol. 28, pp. 611-615 (2010). Control cells were passaged in pieces.

Cell Culture Dish Coating.

Ninety-six-well tissue cell culture plates were coated overnight at 4° C. with sterile solutions of the ECM proteins mouse LN-111 (Invitrogen), human recombinant LN-511, and human recombinant LN-521, all at a concentration of 30 μg/ml (5 μg/cm$^2$). For control cells, BD Matrigel™ hESC qualified (BD Biosciences) was used according to the manufacturer's instructions.

Cell Adhesion Assay.

The assay was performed as described (Extracellular Matrix Protocols, 2000). Briefly, 96-well plates were coated by extracellular matrix proteins as described above and blocked by O3 medium containing bovine serum albumin. The ES cells were plated at a cell density of 600 cell/mm$^2$ upon extracellular matrix-coated plates and were left to adhere for either 1 hour or 1 day at the cell incubator. Non-adherent cells were washed away, and adherent cells were fixed for 20 min by 5% glutaraldehyde, stained by 0.1% Crystal Violet.

Real-Time PCR Quantification of mRNAs.

Total RNA was isolated and cDNA was synthesized as described in Rodin et al., Nature Biotechnol., vol. 28, pp. 611-615 (2010). Real-time quantitative RT-PCR Taqman assays were performed using the Applied Biosystems 7300 Real-Time PCR System. All reactions were done in quadruplicate with predeveloped gene expression assay mix (Applied Biosystems) containing primers and a probe for the mRNA of interest. Additional reactions for each experiment included predeveloped gene expression assay mix for GAPDH, used to normalize the RNA input. All data were analyzed with 7300 System SDS Software version 1.4.

FACS Analysis.

OCT4 expression was analyzed as described in Ludwig, T. E. et al. Derivation of human embryonic stem cells in defined conditions. Nat. Biotechnol. 24, 185-187 (2006). Cells were run on FACSCalibur Flow Cytometer (Becton Dickinson). Data were analyzed with CellQuest software (Becton Dickinson).

Results for Example 1

Figure 4:
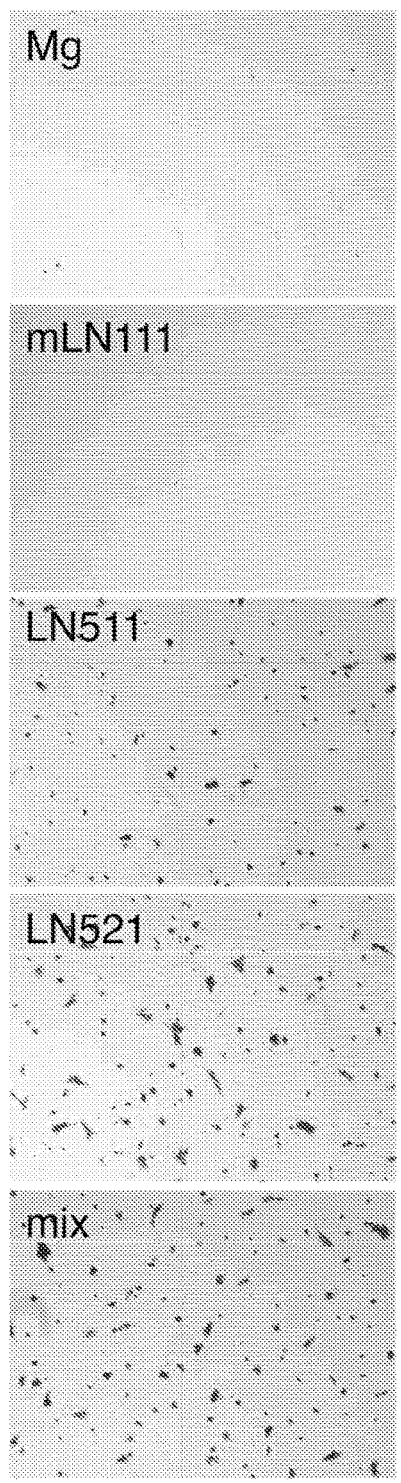
FIGS. 4 and 5 show the Crystal Violet staining of human ES cells adherent to dishes coated in Matrigel (Mg), mouse laminin-111 (mLN111), human recombinant-laminin-511 (r-laminin-511 or r-LN-511), human recombinant-laminin-521 (r-laminin-521 or r-LN-521), or a mixture of r-laminin-511 and r-laminin-521 (mix) after one day in culture. Both Figures are magnified 5×.

To find out how different cell culture coatings affect single cell survival of human ES cells in O3 medium without any additives, we completely dissociated HS181 cells and plated them on either Matrigel, mouse laminin-111, human r-laminin-511, human r-laminin-521, or a mixture of r-laminin-511 and r-laminin-521. The results are seen in FIG. 4. As expected, almost no cells remained attached to Matrigel or mouse laminin-111 by 24 hours after plating. In contrast, the cells on human r-laminin-521, the mixture, and at a less extent on human r-laminin-511 survived.

Figure 5:
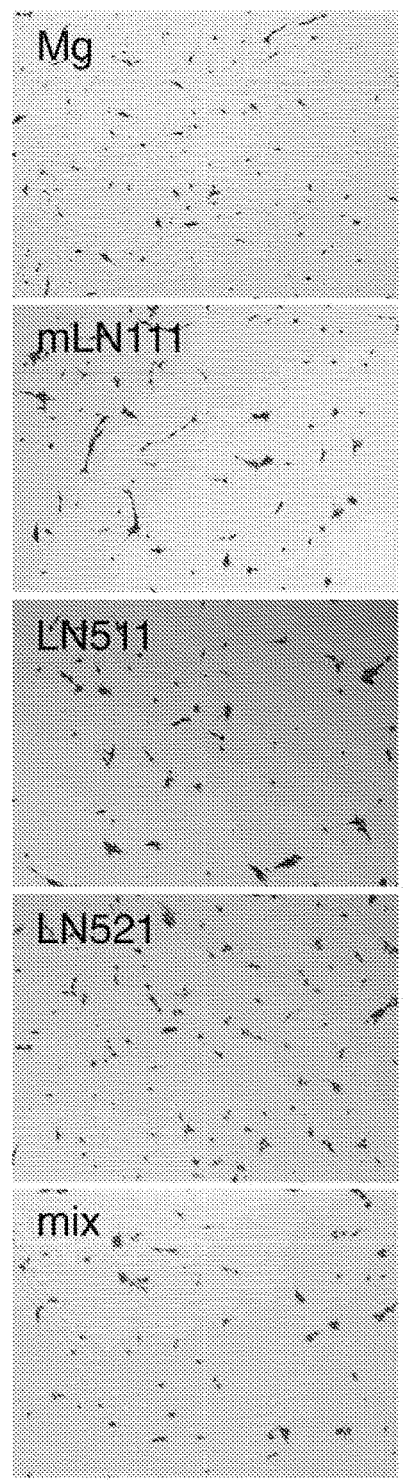

The experiment was repeated on human ES cells in O3 medium treated with ROCK inhibitor Y-27632. These results are seen in FIG. 5. The stem cells remained attached on all 5 coatings.

Figure 6:
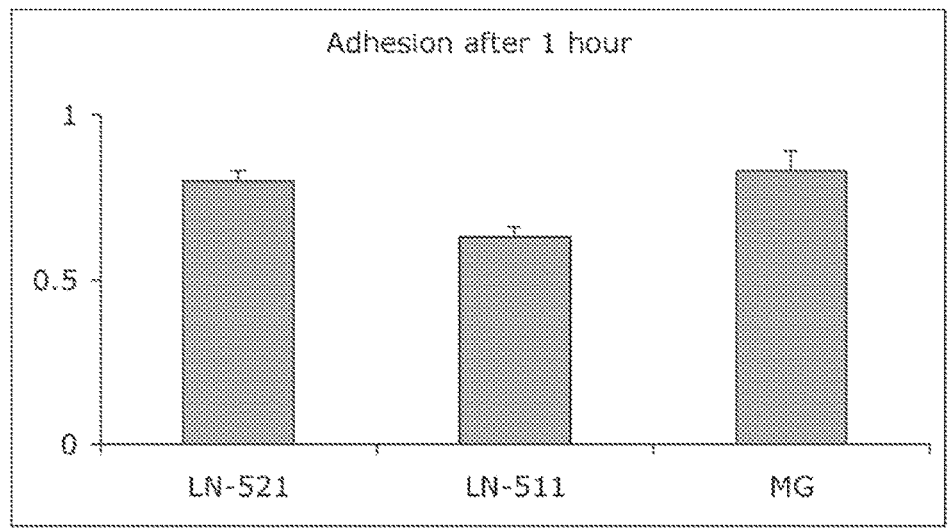
FIG. 6 is a graph showing the adhesion of human ES cells to human r-laminin-521 (labeled as LN521), human r-laminin-511 (LN511), and Matrigel (Mg) coated dishes after one hour in culture without ROCK inhibitor. Error bars show the standard error of measurement. (n=3).

To quantify this effect, we performed cell adhesion experiments on all of the above-mentioned coatings at 1 hour and 1 day after plating (i.e., each of the five coatings, with and without Y-27632). FIG. 6 shows the results for the 1-hour experiment for LN-521, LN-511, and Matrigel (MG) without Y-27632. The adhesion of human ES cells in O3 medium without any additives was roughly the same at this time point.

Figure 7:
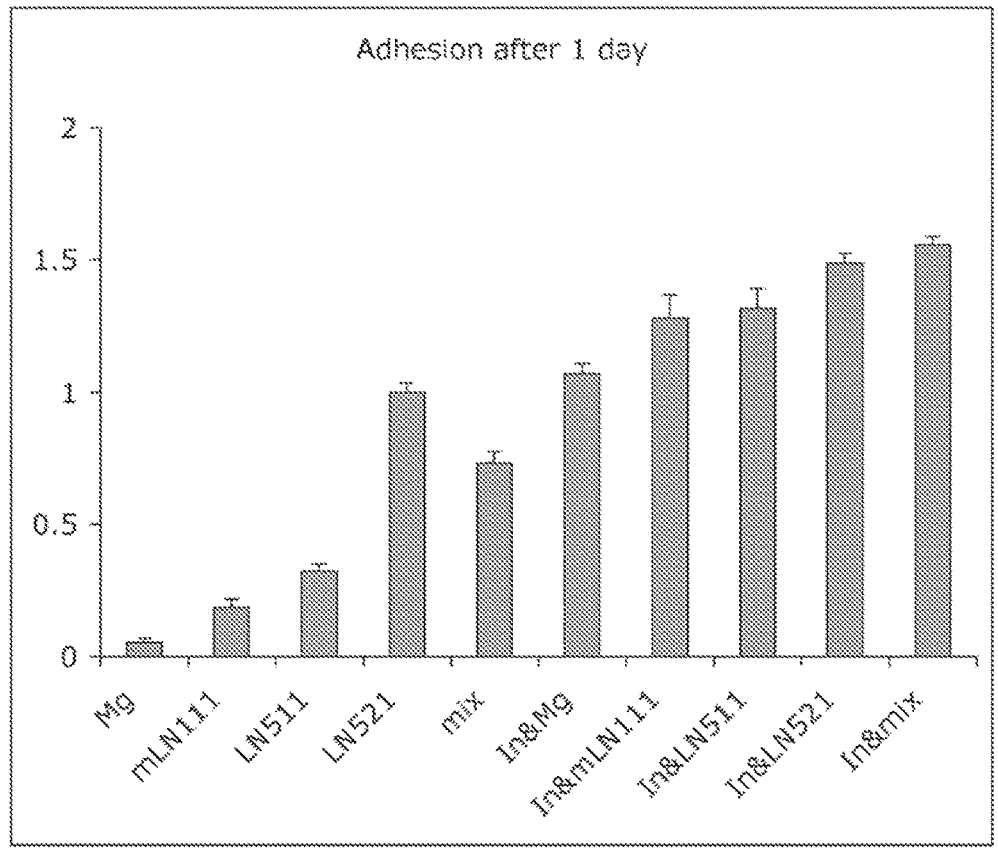
FIG. 7 is a graph showing the adhesion of human ES cells to dishes coated in either Matrigel (Mg), mouse laminin-111 (mLN111), human r-laminin-511 (LN511), human r-laminin-521 (LN521), or a mixture of r-laminin-511 and r-laminin-521 (mix), after one day in culture and without ROCK inhibitor. Also included are results for dishes with ROCK inhibitor and either Matrigel (In&Mg), mouse laminin-111 (In&mLN111), human r-laminin-511 (In&LN511), human r-laminin-521 (In&LN521), or a mixture of r-laminin-511 and r-laminin-521 (In&mix), also after one day in culture. The cells for both experiments were plated at the same density on the same cell culture dish. Error bars show standard error of measurement (n=3).

FIG. 7 shows the results for the 1-day experiment for all of the coatings. The plates containing the Y-27632 inhibitor are labeled as "In&" along with the coating. At 1 day after plating, the stem cells adhered to LN-521 without additives 20 times better than to Matrigel without additives. In addition, the results showed that the adhesion of cells to LN-521 without additives was similar to the adhesion of cells on all dishes including the ROCK inhibitor. In other words, no ROCK inhibitor is necessary with LN-532 coating to obtain results similar to coatings that do contain the ROCK inhibitor.

Figure 8:
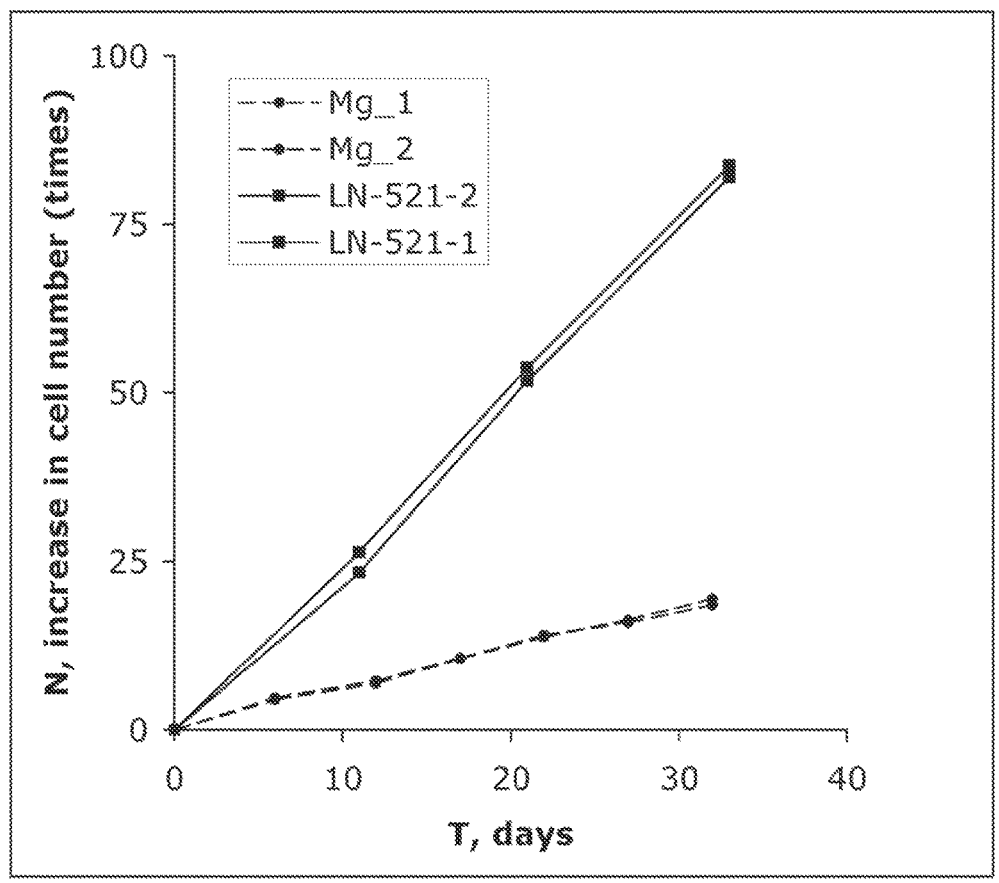
FIG. 8 shows the growth curves for human ES cells cultured on r-laminin-521 (LN-521_1 and LN-521_2) using single cell dissociation passaging and for human ES cells cultured on Matrigel (Mg_1 and Mg_2) using passaging in small clumps. The latter cells were passaged as described in Rodin et al., *Nature Biotechnol.*, vol. 28, pp. 611-615 (2010).

We cultured human ES cells on human r-laminin-521, passaging them after complete dissociation into single cell suspension every 10-12 days in 1:25 to 1:30 ratios. The cells proliferated robustly with a stable and high rate for at least 9 passages (3 months). Moreover, after 3 passages (1 month), they underwent the same number of cell doublings as stem cells after 20 passages (100 days) cultured using conventional methods. This is illustrated in FIG. 8, which shows the increase in the number of cells versus time. The cells on LN-521 increased at a much faster rate than on Matrigel. Thus, the new r-laminin-521 hES cell culture method was advantageous in terms of time and labor.

Figure 9:
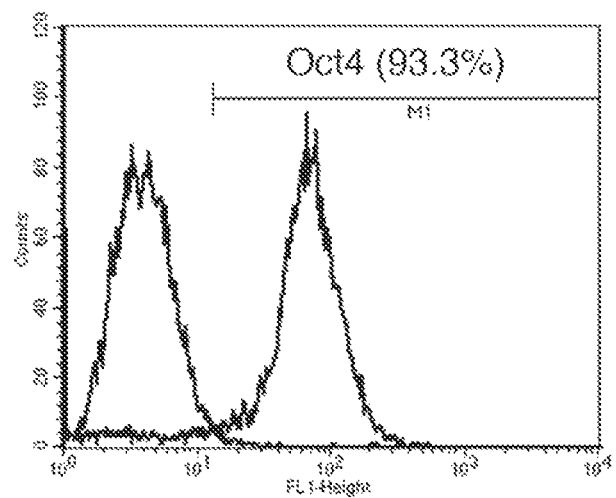
FIG. 9 is a FACS analysis of human ES cells after several single cell dissociation passages on r-laminin-521 for OCT4, a marker of pluripotency. The percentage of positive cells is listed in parentheses.
Figure 10:
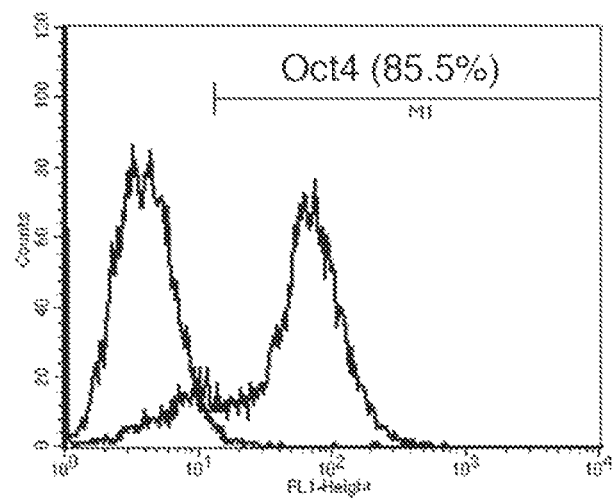
FIG. 10 is a FACS analysis of human ES cells after several passages on Matrigel using splitting in small clumps for OCT4. The percentage of positive cells is listed in parentheses.

To confirm the identity of hES cells after several single cell suspension passages on human r-laminin-521 in O3 medium without any additives, we performed FACS analysis for Oct4, a marker of pluripotency. FIG. 9 shows the results for cells grown on r-LN-521, while FIG. 10 shows the results for cells grown on Matrigel. The percentage of positive cells is listed in parentheses. R-LN-521 had a much higher percentage of pluripotent cells.

Figure 11:
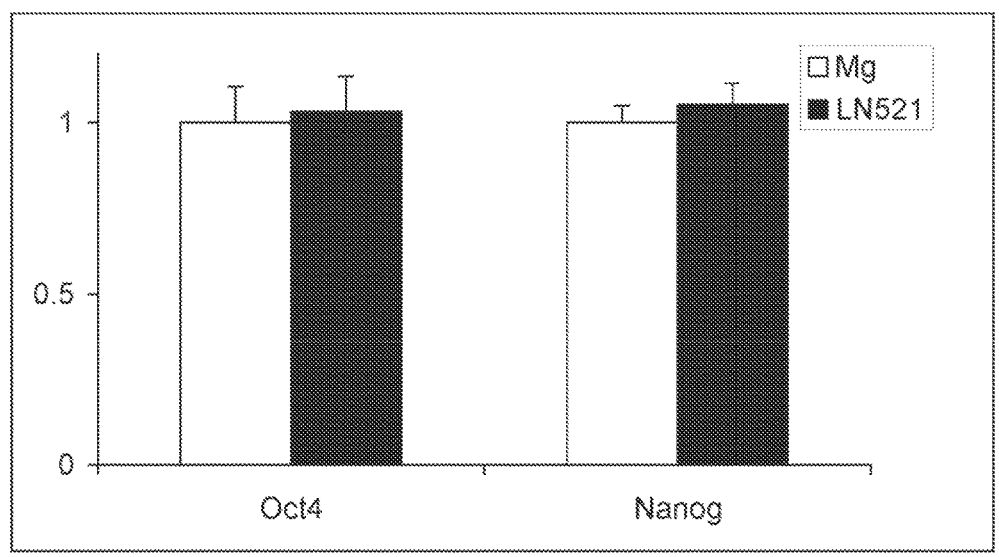
FIG. 11 shows the results of a real-time quantitative RT-PCR analysis which was used to compare numbers of mRNA transcripts of the pluripotency markers Oct4 and Nanog in human ES cells cultured on human r-laminin-521 (LN521) after several single cell dissociation passaging and in the cells cultured on Matrigel (Mg) after several passaging of the cells in clumps. Error bars show 95% confidence intervals.

In addition, the number of mRNA transcripts of the pluripotency markers Oct4 and Nanog was quantified. FIG. 11 shows these results. For both markers, the cells on LN-521 showed higher numbers of transcripts.

Both methods showed that the new methods provides hES cells of the same or better quality than the current method, which uses Matrigel as a cell culture dish coating material and passaging of the cells in small clumps.

Example 2

In this Example 2, expressed and purified recombinant LN-521 that was also expressed in pluripotent hES cells was studied for its effects on cultured hES and iPS cells. The results showed that LN-521, alone, strongly supports self-renewal of pluripotent hES and iPS cells, and, importantly, it allows survival of pluripotent stem cells following plating of trypsinized stem cells in single cell suspension on LN-521 at high dilutions. The effects of LN-521 were shown to be mediated by signaling via α6β1 integrin through induction of hES cell migration and PI3K/Akt pathway activation. The results may be applied for an effective and even automated expansion method for large-scale production of pluripotent hES and iPS cells, as well as for development of new medium formulations for self-renewal of pluripotent stem cells. The new hES/hiPS cell culture method described here closely resembles standard cell culture methods, e.g. that are used to culture fibroblasts, and, therefore, it does not demand special skills. It consumes significantly less cell coating material per one cell division and is time efficient, thus providing significant economical profits in comparison with the previous procedures for culturing hES/hiPS cells.

Human recombinant LN-521, which has previously not been available in pure form, was produced by cloning full-length laminin β2 cDNA and carrying out a triple-transfection of HEK293 cells with the human laminin α5, β2 and γ1 chains. Human recombinant LN-111 and LN-121 were similarly generated following cloning of full-length α1 and β2 chain cDNAs and triple transfection of HEK293 cells with human α1, β1 and γ1 and α1, β2 and γ1 chain cDNAs, respectively. The purified LN-521, LN-111 and LN-121 proteins were shown to contain, respectively, pure α5, β2, and γ1 chains, α1, β1 and γ1 chains, as well as α1, β2 and γ1 chains, as shown by protein staining and Western blot analysis.

Methods

Human ES and iPS Cell Cultures.

Human ES cells of HS181 and HS401 were cultured on LN-521-coated culture dishes in O3 medium (described in Rodin et al., *Nature Biotechnol.*, vol. 28, pp. 611-615 (2010) with pH was adjusted to 7.35), mTeSR1 (STEMCELL Technologies) and chemically defined and xeno-free TeSR2 (STEMCELL Technologies) at 37° C., 5% $CO_2$. Initially, cells of the lines were transferred onto a LN-521 coating from a human feeder cell layer by careful scratching using a sterile knife with subsequent trypsinization, or the cells were trypsinized into single cell suspension from a LN-511 coating. The cells were provided once a day with fresh medium pre-warmed in an incubator for one hour, except for the first day after plating, when only a few drops of fresh medium were added. Cells were routinely passed once in 10-12 days by exposure to Trypsin/EDTA (GIBCO Invitrogen Corporation, Paisley, Scotland) for 5 minutes at 37° C., 5% $CO_2$. They were then gently pipetted to break into single-cell suspension and a Defined Trypsin Inhibitor (GIBCO Invitrogen) was added. The cell suspension was centrifuged at 25 rcf for 4 minutes, the supernatant was discarded, the cell pellet was resuspended in prewarmed O3 medium, and the cells were then passed through a 40 μm sieve. Subsequently, the cells were plated on new LN-521-coated dishes at a concentration of 30,000 cells/cm² in 1:25-1:30 split ratios. Control cells of the same line were cultured on Matrigel (STEMCELL Technologies) and LN-511 in O3 medium as described previously.[9]

For defined and xeno-free cultures, TeSR2 (STEMCELL Technologies) medium and defined free from any animal derived component TrypLE™Select (GIBCO Invitrogen Corporation, Paisley, Scotland) enzyme were used. The cells were passed every 10-14 days by exposure to TrypLE™Select for 4-5 minutes at 37° C., 5% $CO_2$. Then, the enzyme was carefully aspirated and prewarmed TeSR2 medium was added. After that, the cells were gently pipetted to break into single-cell suspension, centrifuged, the supernatant was discarded, and the cell pellet was resuspended in prewarmed TeSR2. The cells were then passed through a 40 μm sieve and plated on a fresh LN-521 coated dish.

Tissue cell culture plates were coated overnight at 4° C. with sterile solutions of the ECM proteins, such as human recombinant LN-521, all at a concentration of 30 μg/ml (5 μg/cm²). Control plates were coated with Matrigel according to the STEMCELL Technologies' instructions. Prior to use, dishes were pre-warmed in an incubator for one hour after which prewarmed O3 medium was added without additional washing of the dish. After applying a fresh LN-521 solution to a new dish, the remaining LN-521 solution could be used at least once more. All the adhesion, survival, and inhibition of survival experiments were carried out using fresh coating materials.

The human iPS cells, ChiPSW line, were derived from lentivirally transduced human foreskin fibroblasts (HFF) with OCT-4/SOX2/NANOG/LIN28 reprogramming genes. The ChiPSW line had normal male karyotype, 46,XY, in repeated testing at different passages. Prior to cell culture and passaging experiments, the cells were first characterized in vitro for expression of pluripotency markers. Immunofluorescence study with antibodies against Oct3/4 (SC-5279), Nanog (SC-33759), TRA-1-60 (SC-21705) and SSEA4 (sc-21704) showed that the cells expressed all those markers of pluripotency. RT-PCR analysis confirmed that the cells lacked expression of the viral transgenes. The pluripotency of ChiPSW cells was confirmed by in vitro (embryoid bodies formation and immunofluorescence study) and in vivo (injection subcutaneously into SCID beige mice) experiments. Cells of ChiSW line could be further differentiated into beating cardiomyocytes. They were also capable of undergoing hematopoietic differentiation.

Before taken to the present feeder free cultures, the iPS cells were maintained and expanded over irradiated human foreskin fibroblasts. Knock-out serum (KSR, Invitrogen)-supplemented media was used for propagation, supplemented with 8 ng/ml of basic fibroblast growth factor (bFGF, R&D Systems). Cells were fed on a daily basis and weekly passaged using collagenase IV (1 mg/ml, Roche) or manual dissection when required.

Prior to these experiments, the CutB1.2 cells were shown to express pluripotency markers Oct4/Nanog/Sox2/TRA-1-60/TRA-1-81, to lack expression of the viral transgenes, and the pluripotency of the cells was confirmed both by in vivo and in vitro differentiation studies.

Laminin-521 and Other Coating Materials.

Human recombinant LN-521, available from BioLamina, AB, Stockholm (www.biolamina.com), was produced in human embryonic kidney cells (HEK293; ATCC CRL-1573) sequentially transfected with full-length laminin γ1, β2 and α5 constructs essentially as described previously. For protein production, the HEK293 cells were cultured in Dulbecco's modified Eagle's medium (DMEM) supplemented with GlutaMax I for up to six days. The LN-521 molecules were affinity-purified using anti-FLAG matrix (Sigma), and then characterized using 3-8% and 4-15% gradient SDS-PAGE under reducing and nonreducing conditions. The proteins were visualized using Sypro Ruby (Bio-Rad) protein staining and immunostaining of the chains on polyvinylidene difluoride membranes. To further characterize the protein, Western blot analysis with antibodies against the laminin α5, β2 and γ1 chains was performed. Human recombinant laminin-111 and laminin-121 were produced similarly to LN-521 and shown to contain the correct chains of predicted molecular sizes by Western and SDS-PAGE. If not otherwise stated, the corresponding mouse laminin-111 (Invitrogen) was indicated as LN-111.

Reagents and Antibodies.

InSolution™ LY 294002 (a specific Akt inhibitor), InSolution™ Wortmannin (a specific PI3K inhibitor), and InSolution™ 98059 (a specific MEK1/Erk inhibitor) were purchased from Calbiochem. Antibodies to phospho-Akt (#4060), total-Akt (#9272), phospho-Erk (#9101), and total-Erk (#9102) were obtained from Cell Signaling Technology. PathScan Phospho-Akt1 sandwich ELISA kit (#7160), PathScan total Akt1 sandwich ELISA kit (#7170), PathScan Phospho-Akt2 sandwich ELISA kit (#7048), and PathScan total Akt2 sandwich ELISA kit (#7046) were also purchased from Cell Signaling Technology. Antibodies to Calnexin (#ab10286) were obtained from Abcam. Function blocking antibodies to various integrin subunits, mouse isotype antibodies, and α-dystroglycan were purchased from Millipore. Since function blocking antibodies to αV (MAB1980) and α6 (MAB1378) were presented in a solution with sodium azide, before the inhibition of survival experiment all the antibodies to alpha integrin subunits were dialyzed thrice against O3 medium for 2 hours each time. Antibodies to Lutheran receptor and α-fetoprotein, as well as rat isotype control antibodies were obtained from R&D Systems. Antibodies to Oct4, Nanog, SSEA-4, smooth muscle actin and MAP-2 were purchased from Millipore.

Immunofluorescence.

For immunofluorescence studies, ES cells were cultured and fixed in 8-well slide chambers (BD Biosciences) or 96-well plate wells by 4% paraformaldehyde, permeabilized by 0.1% Triton-X and blocked by 10% bovine fetal serum (GIBCO Invitrogen Corporation) in phosphate-saline buffer (PBS) containing 0.1% Tween-20 (Sigma-Aldrich, St. Louis, http://www.sigmaaldrich.com) for one hour. Incubation with primary antibody was performed for 1.5 hours at room temperature. Incubation with secondary antibody and 4,6-diamidino-2-phenylindole (DAPI, Molecular Probes) was performed for 40 minutes. Between incubations, the specimens were washed with 0.1% Tween-20 in PBS buffer three to five times. Specimens were preserved in a fluorescence mounting medium (Dako, Glostrup, Denmark, http://www.dako.com), and observed under a fluorescence microscope (Leica, Heerbrugg, Switzerland, http://www.leica.com).

Real-Time PCR Quantification of Different mRNAs.

Total RNA was isolated using Absolutely RNA Microprep Kit (Stratagene, La Jolla Calif., www.stratagene.com) according to the manufacturer's instructions. cDNA was synthesized using 0.2 μg of total RNA in 20 μl reaction mixture, containing oligo(dT)12-18 primers and Superscript II reverse transcriptase (GIBCO Invitrogen Corporation), according to the manufacturer's instructions. Real-time quantitative RT-PCR Taqman assays were performed using the Applied Biosystems 7300 Real-Time PCR System (Applied Biosystems, Foster City, Calif.). All reactions were done in quadruplicates with the use of a pre-developed gene expression assay mix (Applied Biosystems) containing primers and a probe for the mRNA of interest. Additional reactions for each experiment included pre-developed gene expression assay mix for GAPDH for normalizing the RNA input. All data was analyzed with 7300 System SDS Software v 1.4.

FACS Analysis.

Cells were removed from the culture dish with Trypsin/EDTA, dissociated into single cell suspension and resuspended in ice-cold FACS buffer (2% fetal bovine serum, 0.1% sodium azid in Hank's buffer). Incubation with primary antibodies against SSEA-4 (from Millipore, Billerica, Mass., http://www.millipore.com) was performed for one hour on ice. Then, the cells were washed three times with ice-cold FACS buffer. Subsequently, the cells were probed in FACS buffer with 1:400 dilution of Alexa Fluor anti-mouse secondary antibodies (GIBCO Invitrogen Corporation) for 30 minutes in the dark, and washed four times. Control cells were incubated with mouse immunoglobulins and, subsequently, with the secondary antibody as described above. Cells were analyzed on FACSCalibur Flow Cytometer (Becton Dickinson, San Jose, Calif.). Data were analyzed with the CellQuest software (Becton Dickinson).

Karyotyping.

Karyotyping of the cell lines was carried out using standard Q-banding techniques. Samples of cells were treated with colcemid KaryoMAX (0.1 μg/ml; Gibco Invitrogen Corporation) for up to 4 hours, followed by dissociation with Trypsin/EDTA solution (Gibco Invitrogen Corporation). The cells were pelleted via centrifugation and re-suspended in pre-warmed 0.0375 M KCl hypotonic solution and incubated for 10 minutes. Following centrifugation, the cells were resuspended in fixative (3:1 methanol:acetic acid). Metaphase spreads were prepared on glass microscope slides and G-banded by brief exposure to trypsin and stained with 4:1 Gurr's/Leishmann's stain (Sigma-Aldrich Co.). A minimum of 10 metaphase spreads were analyzed and additional 20 were counted.

Teratoma Formation.

Teratoma formation experiments were performed by implantation of approximately $10^6$ cells beneath the testicular capsule of a young (7-week-old) severe combined immunodeficiency (SCID) mouse. Three animals per each cell line were used. Teratoma growth was observed by weekly palpation, and the mice were sacrificed eight weeks after the implantation. The teratomas were fixed, and sections were stained with hematoxylin and eosin (HE) or with hematoxylin, eosin and PAS (HE-PAS). The presence of tissue components of all three embryonic germ line layers was demonstrated, as analyzed from the stained sections. All animal experiments were performed at the infection-free animal facility of the Karolinska University Hospital in accordance with ethical committee approval.

Embryoid Body Formation.

ES cells from LN-521 coated cell culture dishes were exposed to TrypLE™Select for one minute at 37° C., 5% $CO_2$, washes two times with a medium, broken into large pieces and cultured in suspension in low adhesion plates. The medium used for this was Knockout DMEM (GIBCO Invitrogen Corporation) supplemented with 2 mM L-glutamine, 20% fetal calf serum (GIBCO Invitrogen Corporation), 0.1 mM β-mercaptoethanol (GIBCO Invitrogen Corporation) and 1% non-essential amino acids (GIBCO Invitrogen Corporation). After 1-2 weeks in suspension, the embryoid bodies were transferred onto gelatin coated tissue cell culture 96-well plates (Sarstedt), cultured for 1-2 weeks, then fixed, stained with antibodies against markers of all three embryonic germ line layers (smooth muscle actin, MAP-2 and α-fetoprotein) and analyzed as described above for immunofluorescence.

Cell Adhesion Assay.

Briefly, 96-well plates were coated by extracellular matrix proteins as described above and blocked by O3 medium containing bovine serum albumin. The ES cells were plated at cell density of 50,000 cells/cm$^2$ onto extracellular matrix-coated plates and left to adhere for 1 hour in a cell incubator. After that the plates were washed 3 times with the medium to remove the non-adherent cells, and then the adherent cells were fixed for 20 minutes by 5% glutaraldehyde, stained by 0.1% Crystal Violet. (Kebo Lab, Spanga, Sweden, http://www.kebolab.se). After one hour and 3 washes with water, Crystal Violet was extracted with 10% acetic acid and quantified by measuring optical density at 570 nm. All the experiments were performed in quadruplicate.

Cell Survival and Inhibition of Survival Assays.

The survival assay was performed as described for the cell adhesion assay above, except that the cells were left in the cell incubator for 24 hours. For inhibition of survival assay, the cells were kept in a medium with function blocking antibodies at the concentrations recommended by the manufacturer or pathway inhibitors at concentrations indicated in the text for 30 minutes, and then plated on the coated dishes. All the experiments were performed in quadruplicate.

Western Blotting and ELISA.

HS 181 cells were trypsinized into single cell suspension as described above. For inhibition experiments, the cells were kept in O3 medium with blocking antibodies or pathway inhibitors for 30 minutes and then 450K cells were plated on 35 mm dishes precoated with the appropriate matrix coating. For other experiments, same number of cells was plated directly after trypsinization. In all cases the cells were allowed to spread for 1 hour at 37° C., 5% $CO_2$. After two washings in ice-cold PBS, the plates with cells were snap frozen in liquid nitrogen and stored at −80° C. To prepare samples for western blots and ELISA, the plates were slowly thawed and kept on ice with 100-150 μl of lysis buffer (50 mM Tris-HCl, pH7.5, 150 mM NaCl, 0.5% deoxycholate, 0.5% SDS, 1% Triton X-100, 1% Igepal, Complete™ (Roche) and Phospho-Stop™ (Roche)) on top. Then, the cells were scraped, pipetted and sheared through a 27 G ¾" needle. After that, the cell pellets were clarified by centrifugation at 16,100 rcf for 15 minutes at 4° C. For western blots, 4-12% gradient gels were used for SDS electrophoresis and the proteins were transferred to PVDF membranes. The membrane was hybridized with the antibody of interest according to the manufacturer's instructions. Chemoluminescent HRP-substrate from Amersham Biosciences was used for visualization. For the densitometry analysis the films were scanned at 2,400 dpi and analyzed by the Chemilmager5500 program (1 D-Multi Line densitometry mode). For ELISA the samples were applied to the wells according to the manufacturer's instructions.

In Vivo Imaging and Migration Assay.

24-well plates were coated by extracellular matrix proteins and blocked by O3 medium containing bovine serum albumin. The ES cells were plated at cell density of 30,000-40,000 cells/cm$^2$ onto extracellular matrix-coated plates and left to adhere for half an hour in a cell incubator. After that, the plate was transferred into high content imaging system Operetta (PerkinElmer) equipped with environmental control unit, which allowed to keep 37° C., 5% $CO_2$. For two movies that were made, the brightfield images were taken once in 15 minutes during 24 hours after plating using Harmony software (PerkinElmer), exported, and analyzed using ImageJ software (NIH, the US). For migration assay the images were taken every seven minutes during 18 hours after plating. Images acquired between the fifth and seventh hours after plating were analyzed using MTrackJ plug-in (University Medical Center, Rotterdam, The Netherlands). 100 attached cells on each coating were traced and mean distances from the current to the previous point of the track were calculated. Error bars show standard error of the mean s.e.m. (n=100).

Statistics.

Statistical significance was determined the by Student's two-tailed t-test for unequal variances.

Discussion of Results for Example 2

Pluripotent hES cells express α1, α5, β1, β2 and γ1 laminin chains. To compare the adhesion and clonal survival of hES cells plated from single cell suspension to different coating substrata, hES cells growing as monolayers on LN-511 or as clusters on a feeder layer were trypsinized into single cell suspension in O3 medium and plated on cell culture dishes coated with Matrigel, LN-111, LN-511, LN-521 or a mixture of LN-511 and LN-521, in the absence or presence of a ROCK inhibitor (Y-27632) and analyzed after 24 hours.

The cells did not survive on Matrigel or LN-111, but they did so as single cells on human recombinant LN-511 and LN-521, as well as on the mixture of the two. However, the survival of cells on LN-521 was significantly higher than on LN-511 (compared in numbers below). Cells plated on human recombinant LN-111 or LN-121 failed to survive after 24 hours (data not shown), which demonstrates that the presence of the β2 chain in a laminin trimer, as such, is not sufficient to support the effect. In the presence of ROCK inhibitor Y-27632, the hES cells survived on all surfaces.

There were, however, clear differences with regard to cell shapes between cells growing on LN-521 in the absence or presence of ROCK inhibitor 24 hours after plating. In the absence of ROCK inhibitor 24 hours after plating, cells growing on LN-521 were round, while the cells growing in the presence of ROCK inhibitor adopted spindle or crescent like shape possibly caused by rearrangement of the actin cytoskeleton.

To test if LN-521 could be used as a cell coating material for long-term self-renewal of human pluripotent cells, HS181, HS401, H1 cells and human iPS ChiPSW and CutB1.2 cells were cultured on the protein in O3, mTeSR1 or TeSR2 media. Cells growing in O3 or TeSR1 media were passed in single cells suspension every 10-14 days at ratios of 1:20-1:30. Pluripotent hES cells proliferated at a stable rate similar or higher to that of cells grown on LN-511 or Matrigel when passed in small clumps. Thus, one passage on LN-521 yielded the same or higher number of cell divisions than that of control cells passed twice in clumps. HS181, HS401, and H1 cells proliferated for at least 24, 5 and 15 passages, respectively (9, 2 and 6 months) in an O3 medium. CutB1.2 iPS and ChiPSW cells have been cultured for 5 and 3 passages in mTeSR1, respectively. Interestingly, dissociated hES cells could be cultured on LN-521 under completely defined and xeno-free conditions, using TeSR2 medium and TrypLE Select enzyme. The plating efficacy after a passage was slightly lower than that of the cells in O3 or mTeSR1 media, and the dissociated cells were passed normally every 10-14 days in 1:15-1:20 ratios. H1 and HS401 cells have been cultured for 12 and 4 passages, respectively (5 and 1.5 months) in TeSR2.

The hES cells were usually plated in single cell suspension at 30,000 cells per 1 cm² of culture dish coated with LN-521, after which individual cells lacked any direct contacts with each other. Eight hours after plating, the hES cells could be observed as single cells expressing pluripotency markers Oct4, Nanog, and Sox2. Twenty four hours after plating, the cells formed small monolayer colonies that eventually combined into large islands of monolayers covering most of the well.

Cells grown on LN-521 showed stable expression levels of pluripotency markers Oct4, Nanog, and SSEA4, which were similar to those in cells plated on Matrigel and passed as small clumps. To compare the level of spontaneous differentiation in LN-521 and Matrigel cultures, the amount of mRNAs for differentiation markers PAX6, SOX17 and SOX7 expressed in Matrigel cultures and in LN-521 cultures were compared after one (10 days) and 10 passages (4 months). Quantitative RT-PCR revealed similar or less levels of expression of all three markers of differentiation in LN-521 cultures independently on the passage number.

Karyotypes were confirmed to be normal for hES cell lines HS181 and H1 after 12 and 10 passages, respectively, on LN-521 in the O3 medium; and for H1 after 7 passages in TeSR2 medium. Histological examination of teratomas formed in SCID mice after injection of HS181 and H1 cells cultured for 13 and 12 passages, respectively, on LN-521 in O3 medium, and H1 cells cultured for 7 passages on LN-521 in TeSR2 revealed development of tissues containing all three germ lineages of the human embryo. Differentiation in vitro also revealed, that the cells in all three cases retained the competence to form embryoid bodies expressing markers of mesoderm (smooth-muscle actin), ectoderm (MAP-2) and endoderm (α-fetoprotein).

To quantify the efficacy of the coating substrata, adhesion after one hour and survival after 24 hours of dissociated hES cells on Matrigel, LN-111, LN-511, LN-521, and an equal mixture of LN-511 and LN-521 were studied. Interestingly, after one hour about the same 75-80% of cells had adhered to all the coatings, although the spreading of the cells was clearly better on LN-521 and LN-511 than on Matrigel or LN-111 (not shown). After 24 hours, almost no cells had survived on Matrigel or LN-111, and very few on LN-511. In contrast, the survival of hES cells on LN-521 was approximately 20 times higher than on Matrigel, and three times higher than on LN-511.

To qualitatively compare the effects of LN-521 and ROCK inhibitor (Y-27632), we plated cells from the same single cell suspension at the same plating density (40,000 cells per 1 cm²) in a medium containing 10 µM of Y-27632 and studied their survival on the different coatings. The untreated cells on LN-521 and Y-27632 treated cells on Matrigel showed similar survival rate 24 hours after plating. Interestingly, even Y-27632 treated human ES cells survived better on LN-521 than on Matrigel.

If exogenous bFGF was removed from the O3 medium, the cells still showed 20 times higher survival on LN-521 than on Matrigel. Moreover, hES cells survived on LN-521 24 hours after plating, even in a medium lacking all the growth factors of the TeSR1 formulation (bFGF, LiCl, γ-aminobutyric acid (GABA), pipecolic acid and TGFβ)[16], suggesting that the survival mechanism is independent of signaling induced by those factors.

An assay for inhibition of cell survival using function-blocking antibodies to potential receptors for LN-521 on the plasma membrane showed that antibodies to integrins α6, and to a slightly lesser extent to β1, inhibited survival of human ES cells on LN-521. Function-blocking antibodies to other tested integrin subunits, as well as to Lutheran receptor and α-dystroglycan, showed very little if any effects on human ES cell survival on LN-521.

Figure 12:
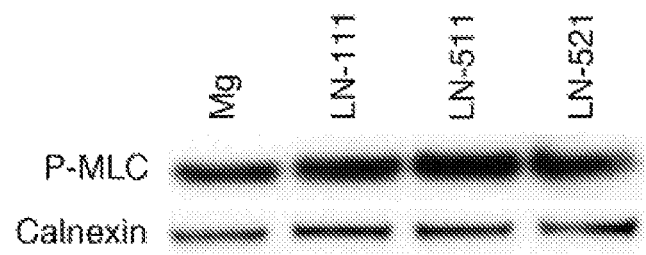
FIG. 12 is a Western blot comparing the levels of phosphorylated myosin light chain (P-MLC) in stem cells grown on Matrigel (Mg), LN-111, LN-511, and LN-521 one hour after plating.
Figure 13:
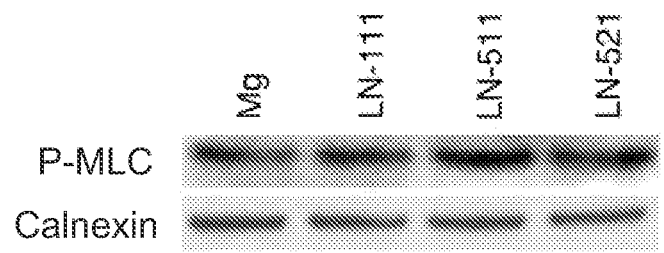
FIG. 13 is a Western blot comparing the levels of phosphorylated myosin light chain (P-MLC) in stem cells grown on Matrigel (Mg), LN-111, LN-511, and LN-521 six hours after plating.
Figure 14:
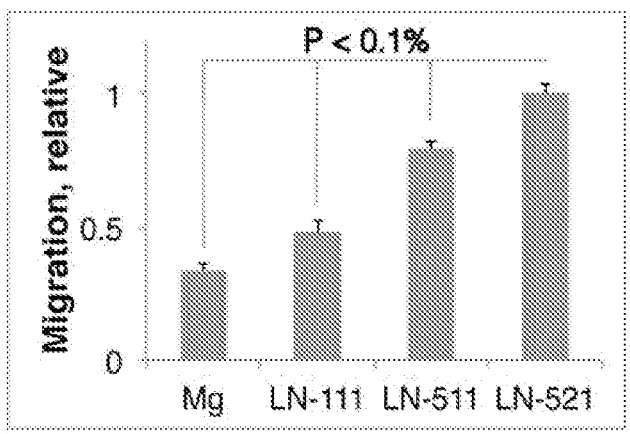
FIG. 14 is a graph comparing the relative migration of human embryonic stem cells grown on Matrigel (Mg), LN-111, LN-511, and LN-521 between five and seven hours after plating.
Figure 15:
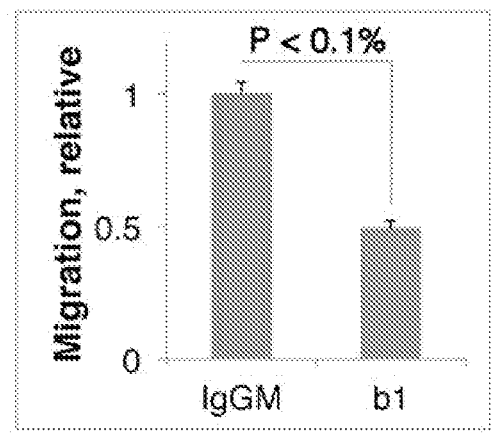
FIG. 15 is a graph comparing the relative migration of human embryonic stem cells grown on LN-521 with IgG and IgM blocking antibodies applied (IgGM) and with a function blocking antibody to integrin β1 (b1) applied. This shows that blocking the integrin significantly reduced motility.

Recently, it has been shown that ROCK inhibitors and blebbistatin act through abrogation of actin-myosin contractility, which is mediated by phosphorylation of the myosin light chain (MLC). To test if LN-521 had similar activity, levels of phosphorylated MLC were compared between the dissociated cells on Matrigel, LN-111, LN-511, and LN-521 one and six hours after plating (FIG. 12 and FIG. 13). Interestingly, western blot showed that phosphorylation of MLC was even higher in the cells on LN-511 and LN-521 than that in the cells on Matrigel and LN-111. Since actin-myosin rearrangements are essential not only for contractions, but also for cell motility, we surmised that the cell migration could be caused by interaction between LN-521 and its integrin receptor α6β1. In vivo imaging of the cells on Matrigel and LN-521 revealed that the cells migrated much faster on the latter and survived by aggregation into small fast moving colonies. Migration of hES cells on the four coatings was also compared between the fifth and seventh hours after plating when the cells were still attached in all cases (FIG. 14). Motility of the hES cells on LN-521 was higher than that of the cells on other coatings and correlated with the ability to survive on them. Treatment with function blocking antibody to integrin β1 significantly reduced motility (FIG. 15) and adhesion (data not shown) of the cells on LN-521.

Figure 16:
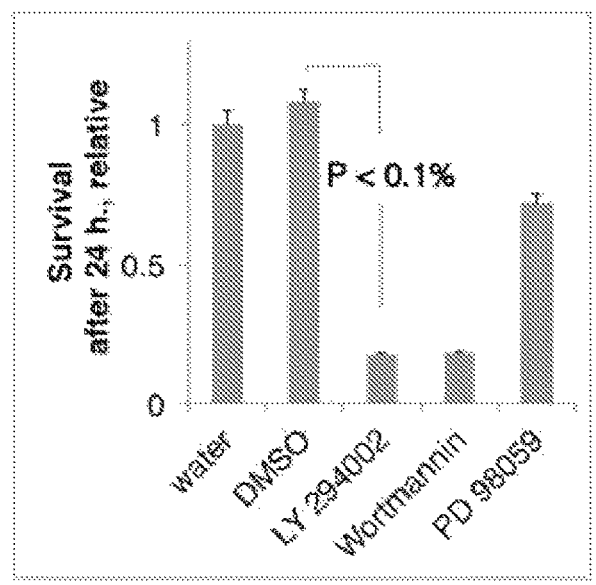
FIG. 16 is a graph comparing the relative survival of hES cells on LN-521 in the presence of water, DMSO, LY294002 (Akt inhibitor), wortmannin (PI3K/Akt inhibitor), and PD 98059 (MEK1 inhibitor). This showed that activation of PI3K/Akt was necessary for hES cell survival on LN-521. The medium contained bFGF.

An extensive body of data has shown that activation of the MEK1/Erk or PI3-kinase/Akt pathways by integrins can block anoikis. The effects of LY 294002 and PD 98059, specific inhibitors of Akt and MEK1, respectively, were examined to explore the potential role of these pathways in hES cell survival on LN-521. Blockade of Akt activation by LY 294002 was found to facilitate detachment and hES cell death, with no cells surviving 24 hours after plating on LN-521 (FIG. 16). In contrast, treatment with PD 98059 did not affect the survival that severely. hES cells treated with another PI3K/Akt specific inhibitor, Wortmannin, also failed to survive 24 hours after plating on LN-521, confirming that activation of PI3K/Akt was necessary for the cell survival on LN-521.

Figure 17:
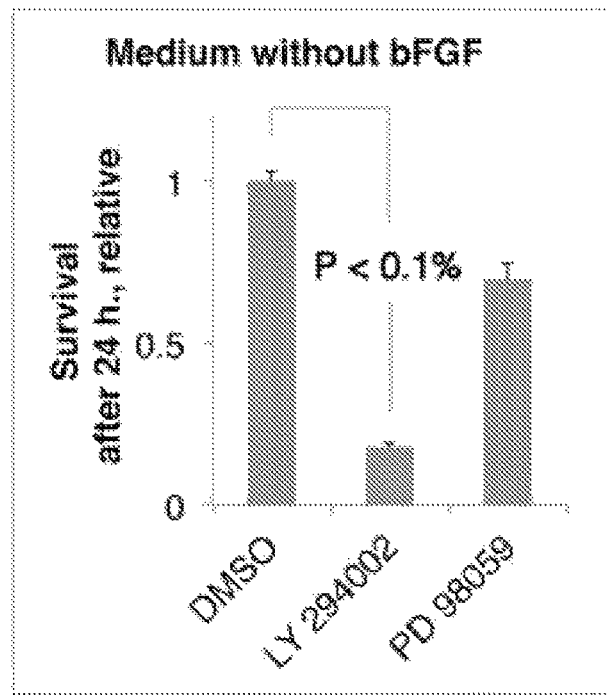
FIG. 17 is a graph comparing the relative survival of hES cells on LN-521 in the presence of DMSO, LY294002 (Akt inhibitor), and PD 98059 (MEK1 inhibitor). No exogenous bFGF was present.
Figure 18:
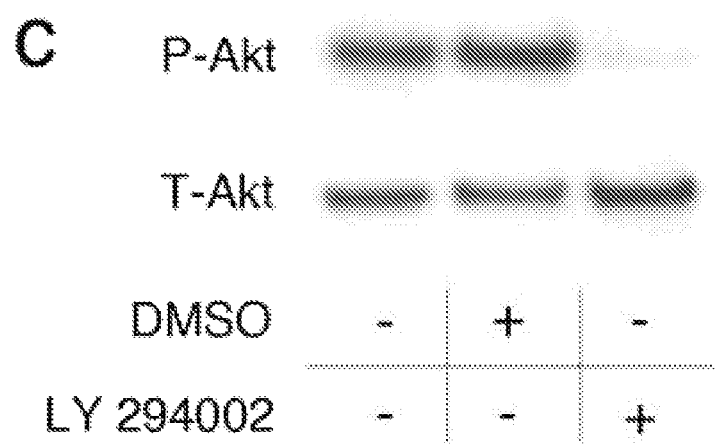
FIG. 18 is a Western blot comparing cells treated with LY 294002 against control cells (DMSO) and collected one hour after plating on LN-521.
Figure 19:
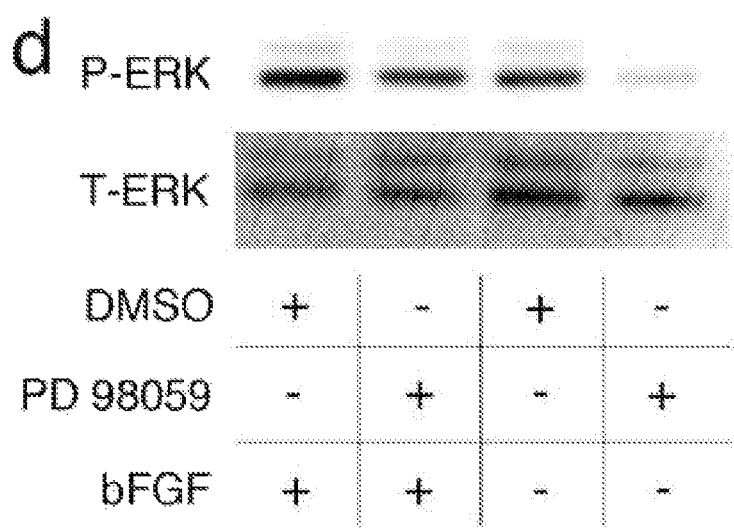
FIG. 19 is a Western blot comparing cells treated with PD98059 against control cells (DMSO) and collected one hour after plating on LN-521.

Since bFGF is known to be a potent activator of the MEK1/Erk pathway, the influence of which cannot be fully inhibited by PD 98059, we performed the same experiment in O3 medium without exogenous bFGF with the same result (FIG. 17). The efficacy of LY 294002 and PD 98059 treatment was confirmed by western blot analysis of the treated and control cells collected one hour after plating on LN-521 (FIG. 18 and FIG. 19).

Figure 20:
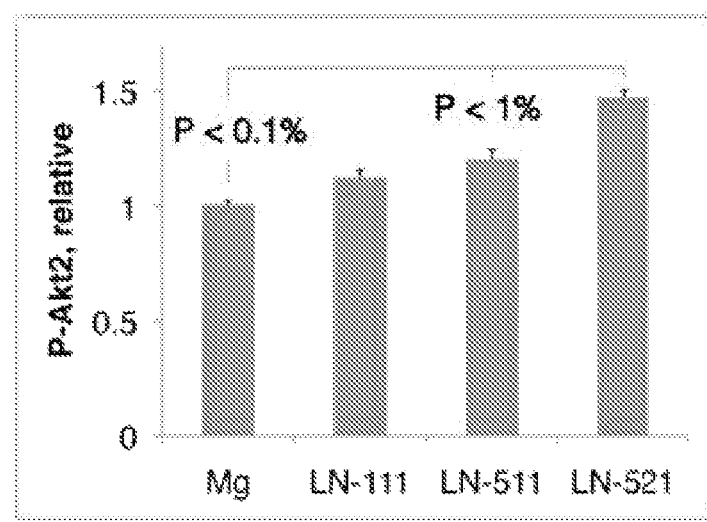
FIG. 20 is a graph showing the relative levels of Akt2 phosphorylation on cell lysates collected one hour after plating on Matrigel (Mg), LN-111, LN-511, or LN-521, obtained using ELISA.
Figure 21:
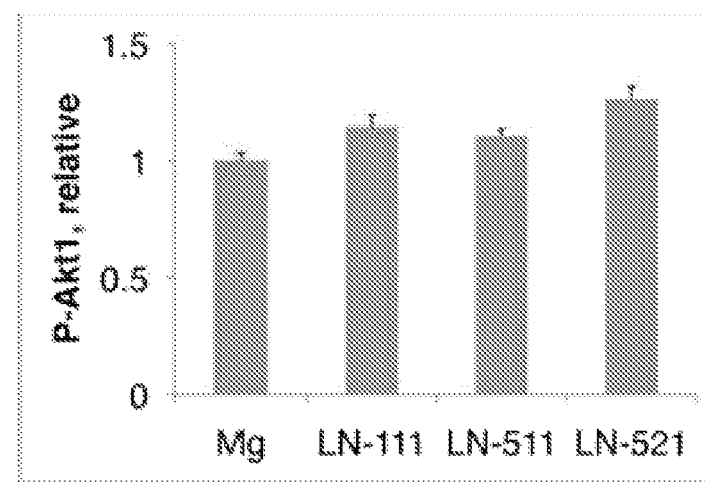
FIG. 21 is a graph showing the relative levels of Akt1 phosphorylation on cell lysates collected one hour after plating on Matrigel (Mg), LN-111, LN-511, or LN-521, obtained using ELISA.

Western blot analysis of extracts of cells growing on Matrigel and LN-521 with antibodies to phospho-Akt showed that the PI3K/Akt pathway was active in both cases (data not shown). To determine the levels of Akt activation in the cells on different coating, ELISA was performed on cell lysates collected one hour after plating on Matrigel, LN-111, LN-511 and LN-521 when the cells still did not have direct contacts with each other (FIG. 20 and FIG. 21). The level of Akt2 phosphorylation in the cells on different coatings correlated with survivability on them.

It has been demonstrated that α6 and β1 integrins are the most abundantly expressed integrin isoforms in human ES cells among alpha and beta subunits respectively. Integrin α6β1 shows a broad spectrum of specificity towards different laminins, but the binding affinity for LN-521 or LN-511 is higher than that for LN-111. Recently, it has been established that β2 laminins have higher affinity for integrins than the β1 laminins. Therefore, having the highest affinity for the integrin, LN-521 can provide the best anchorage for migration and can convey the highest dose of signal via α6β1 integrin resulting in the best survivability of dissociated pluripotent hES cells, although e.g. LN-511 also can do it at a lesser extent.

The results of this work may facilitate culturing and expansion of pluripotent human stem cells in general, and even make automated expansion of such cells possible including cell aimed for clinical applications. The survival of dissociated hES cells on LN-521 appears to be dependent on migration and the cells can therefore not survive after plating at ultralow densities. The new hES cell culture method described here utilizes only a naturally occurring LN-521 adhesion protein that does not damage the cytoskeleton as ROCK inhibitor or blebbistatin treatment do. Thus, LN-521 most probably favors survival of the cells only with the correct integrin profile on the cell surface. The present results also showed that hES cells plated on LN-521 at relatively low densities of 20,000-30,000 cells per 1 cm$^2$ could survive and multiply at least as efficiently as in the other hES culture systems. The new method closely resembles standard cell culture procedures, e.g. culturing of fibroblasts, and, therefore, hES cell cultures on LN-521 do not demand specially trained personnel, which has been a major problem before since culturing of hES cells has been a technological challenge.

The widely used TeSR1 formulation for human pluripotent stem cell self-renewal was initially developed for use with Matrigel and it contains high doses of bFGF that mostly targets the MEK1/Erk pathway, which is not widely considered to have a beneficial effect for pluripotent hES cells. The present results can lead to development of new medium formulations utilizing benefits of LN-521 as coating material and specifically targeting pathways, which are important for human ES cell self-renewal.

In summary, the present work has demonstrated that LN-521, normally secreted by pluripotent hES, can as a sole coating material support self-renewal of human pluripotent stem cells in culture, similar to LN-511. Both laminins facilitated growth of the cells as homogenous monolayers in vitro. However, an important difference between the two laminins is that hES/hiPS cells could be trypsinized into single cell suspension, and plated and effectively expanded from single cells on LN-521, as opposed to manual splitting of cell clusters, as is currently required for expansion of hES/iPS cells grown on Matrigel or feeder cells. The results of this work may facilitate culturing of pluripotent human stem cells and facilitate automated expansion of such cells.

Example 3

Human embryonic stem cells were cultured upon a laminin-521 substrate in two different cell culture mediums. The two cell culture mediums differed in the amount of bFGF, 3.9 ng/ml and 100 ng/ml.

Figure 22:
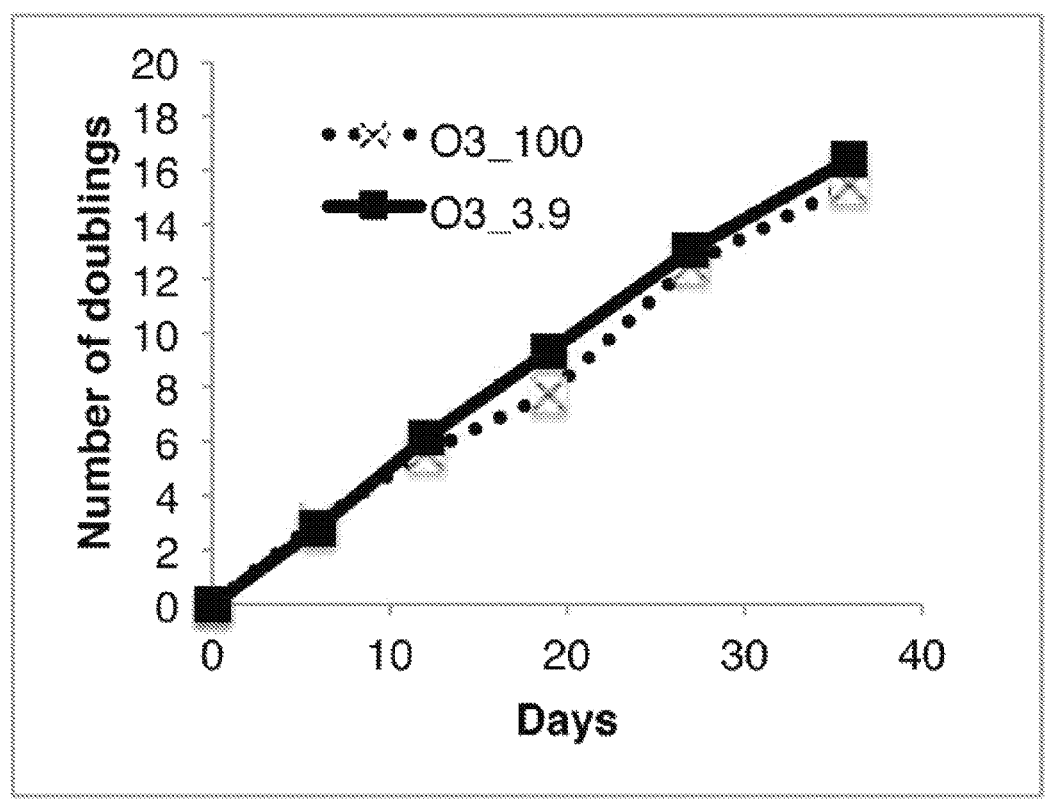
FIG. 22 is a graph showing the growth curve of HS181 hES cells cultured in a low bFGF medium (O3_3.9) compared to a higher bFGF medium (O3_100).

FIG. 22 shows the growth curve of HS181 hES cells cultured in an O3 medium comprising 3.9 ng/mL of bFGF with a laminin-521 substrate after 5 passages (40 days) in solid black. The O3 medium was a variant of the commercially available chemically defined mTeSR1 medium with bovine serum albumin as the only animal derived component. The growth curve of HS181 hES cells cultured in an O3 medium comprising 100 ng/mL of bFGF with a laminin-521 substrate is shown in dashes. The cells were dissociated into single cell suspension for passaging. As seen here, the growth curve for the lower amount of bFGF was as good as or better than the higher amount of bFGF.

Figure 23:
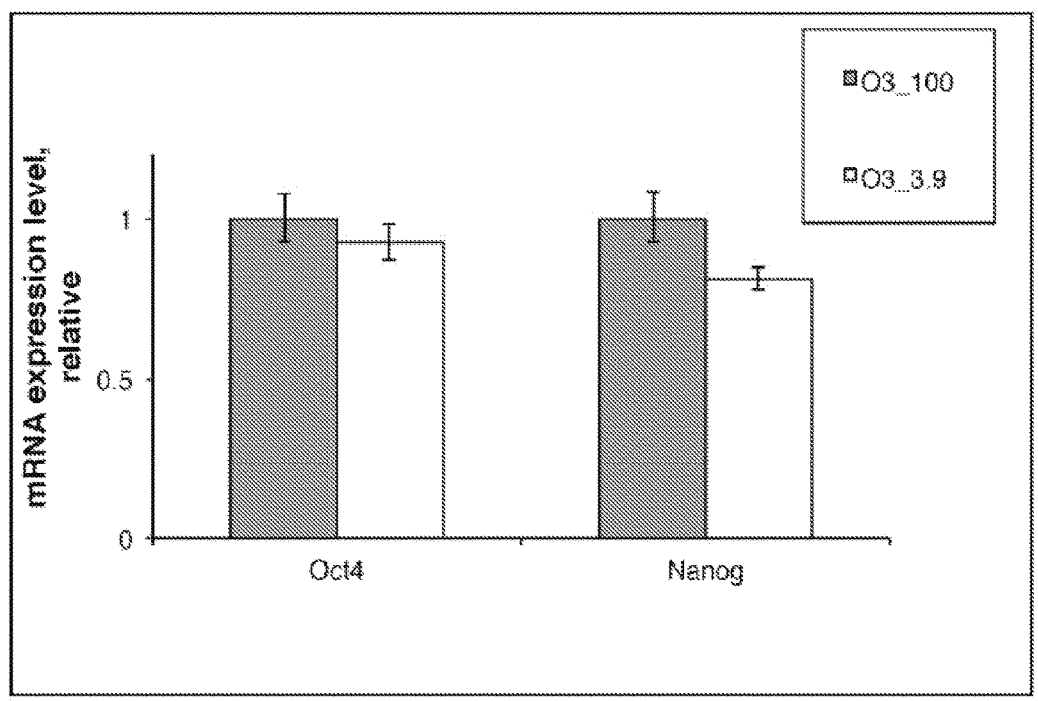
FIG. 23 is a graph showing the relative mRNA expression level for two pluripotency markers (Oct4 and Nanog) in HS181 hES cells cultured in a low bFGF medium (O3_3.9) compared to a higher bFGF medium (O3_100).

FIG. 23 shows the relative amount of mRNA transcripts for pluripotency markers Oct4 and Nanog after 5 passages (40 days) for both media, which was obtained using real-time quantitative reverse transcription polymerase chain reaction (RT-PCR) analysis. Again, similar amounts were obtained in both cell culture mediums, indicating that the stem cells in the lower amount of bFGF maintained pluripotency. Thus, a lower amount of bFGF can be used and still obtain good results, particularly in combination with the laminin-521 substrate.

Example 4

In Examples 1 and 2, the dissociated stem cells survived mostly through active motility on LN-521 and association into small effectively growing and migrating monolayer islands. The cells plated at very low, cloning densities died through anoikis, a specialized from of programmed cell death. Normally, integrin-related signaling from extracellular matrix molecules, e.g. laminins, and cadherin-related cell-cell signaling, can prevent anoikis. The most abundant cadherin isoform on the human ES cell surface is epithelial-cadherin (E-Cadherin). The experiments in Examples 3 were performed to find out if a combination of LN-521 and E-Cadherin could protect human ES cells from anoikis and allow clonal survival of the cells.

hES cells were plated in mTeSR1 medium on different coatings at a density of 250 cells per cm$^2$ and monitored after 5 days in culture using an alkaline phosphatase staining kit. Neither laminin-521 nor E-Cadherin alone permitted efficient clonal survival of individualized hES cells.

Next, combinations of laminin-521 and E-Cadherin were tested to determine whether the combinations could sustain clonal survival of the cells. Fixed amounts of laminin-521 were used for the cell culture dish coating in combination with titrated E-Cadherin. Clonal survival of cells was achieved at different ratios of E-Cadherin to laminin-521 including from about 1:10 w/w to about 1:5 w/w.

Additional tests were performed to test the effects of various modifications to the mTeSR1 medium. A mixture of E-Cadherin to laminin-521 in a ratio of about 1:10 w/w was used to coat the plates. Unexpectedly, it was discovered that a 2× increase in albumin concentration significantly improved clonal survival of hES cells on the laminin-521/E-Cadherin matrix. The rate of individualized hES cell survival under these conditions was from 10 to 15% and was at least one order of magnitude higher than that of the cells on Matrigel, laminin-521, or E-Cadherin alone in both mTeSR1 medium and mTeSR1 medium with additional albumin. Time-lapse photography of the cells confirmed that laminin-521/E-Cadherin coatings facilitated cell survival through proliferation of the single cells, not through the aggregation of different cells. Laminin-521/E-Cadherin similarly sustained clonal survival of cells in completely chemically defined and xeno-free TeSR2 medium with the addition of recombinant human serum albumin (rHSA).

In additional testing, hES cell lines were derived. Twenty-four well tissue cell culture dish plates were washed twice with Dulbecco's Phosphate Buffered Saline. Next, the dish plates were coated for 2 hours at 37° C. with sterile solution containing: 48 μL of 100 μg/mL laminin-521 (BioLamina AB, Stockholm); 6 μL of 82 μg/mL E-Cadherin (R@DSystems); and 300 μL of DPBS with calcium and magnesium (GIBCO) to produce a laminin-521/E-Cadherin matrix.

The donated embryos used to derive the hES cell lines were obtained from an accredited in vitro fertilization clinic after the consent of both partners and ethics approval were obtained. Only fresh or frozen embryos, which could not be used for infertility treatment, were used in the derivation procedures. One or two cells were isolated from an 8-cell stage embryo using a micropipette after making a small opening to the zona pellucida with a laser apparatus designed for this purpose. This procedure has been accredited for clinical use in pre-implantation genetic diagnostics (PGD). The cells were placed on the laminin-521/E-Cadherin matrix in TeSR2 medium with additional rHSA. The cells successfully attached and started to proliferate. The parental embryos were allowed to grow to a blastocyst stage and frozen. The embryo culture was carried out using xeno-free standardized in vitro fertilization culture media in drops under oil at 37° C. and 5% $O_2$/10% $CO_2$. After removal of the zona pellucida, the inner cell masses of five human blastocysts were mechanically isolated and plated in 4-well culture plates (Nunc) onto the laminin-521/E-Cadherin matrix. Following an initial 48 hours of culture, the culture medium was replaced on a daily basis. After 10 to 14 days, the outgrowths were mechanically isolated and replated onto laminin-521/E-Cadherin matrix. Mechanical passaging was used for the subsequent 2 to 3 passages after which colonies were passaged using TrypLE Select (GIBCO).

Figure 24:
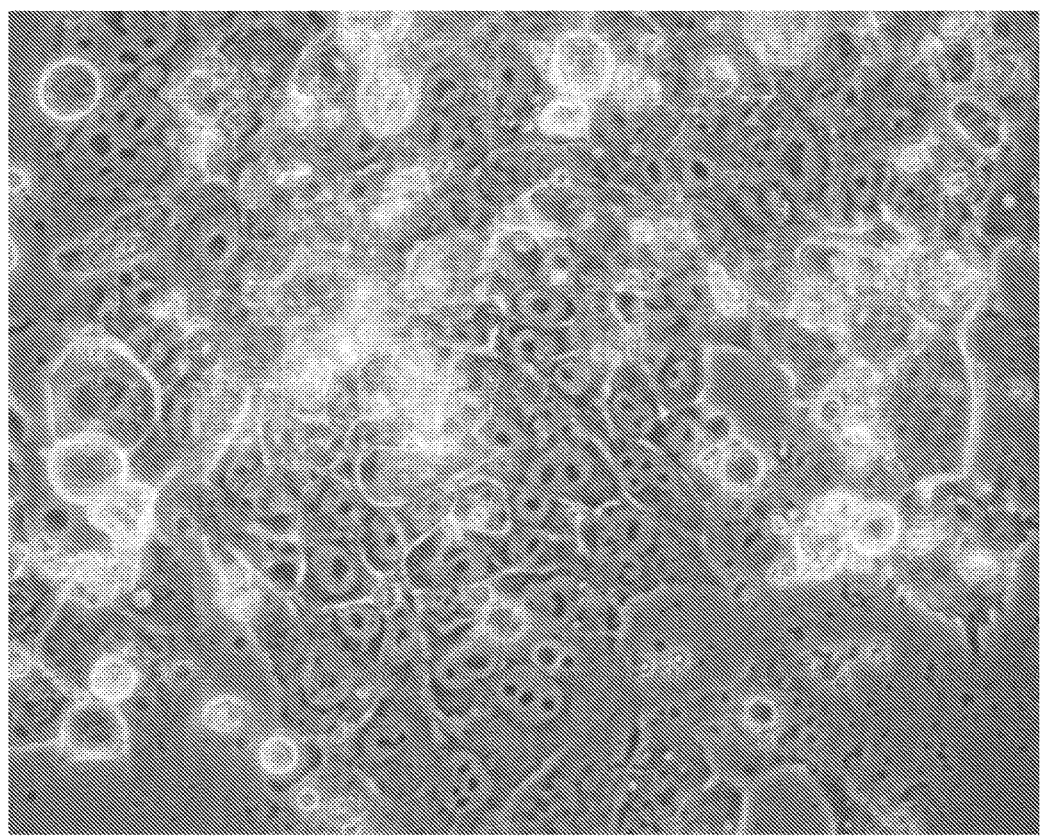
FIG. 24 is a picture showing an early stage derivation of a new human embryonic stem HS841 cell line on laminin-521/E-Cadherin matrix.

Using the laminin-521/E-Cadherin matrix described above with the mTeSR1 medium including additional bovine albumin, three new hES cell lines were derived from six cultured blastocysts. Four days after plating, the inner cell masses gave stem cell-like outgrowths. FIG. 24 shows an early stage derivation of a new human embryonic stem HS841 cell line on laminin-521/E-Cadherin matrix. Morphologically typical human embryonic stem cells growing out from the inner cell mass of a day six blastocyst four days after mechanical isolation of the inner cell mass and plating on laminin-521/E-Cadherin matrix are shown.

Unexpectedly, the cell culture system and method gave stable, hES cell lines in 3 out of 6 embryos (50%), a derivation rate higher than that of standard methods.

The use of a laminin-521/E-Cadherin matrix and TeSR2 medium with additional rHSA, a completely chemically defined and xeno-free environment, yielded similar results in the derivation of new hES cell lines.

Table 5 below provides the formulation for the mTeSR1 medium used in this Example. The amounts of each ingredient can vary by up to 20%.

In particular embodiments, the amount of human serum albumin (HSA) can be varied from a concentration of 0.195 mM to 1 mM, including from 0.3 mM to 1 mM or from 0.3 mM to about 0.4 mM. The amount of bFGF can also be varied from 0 to about 105 ng/mL, or from 0 to 3.9 ng/mL, or from 0.5 ng/mL to 3.5 ng/mL. These two variations in the amount of HSA and bFGF may occur independently or together.

TABLE 5 mTeSR1 formulation.

| mTeSR1 Ingredient | molar mass (g/mol) | Concentration (ng/mL) | Concentration (mM) |
|---|---|---|---|
| INORGANIC SALTS | | | |
| Calcium chloride (Anhydrous) | 110.98 | 9.14E+04 | 8.24E-01 |
| HEPES | 238.3 | 2.81E+06 | 1.18E+01 |
| Lithium Chloride (LiCl) | 42.39 | 4.15E+04 | 9.80E-01 |
| Magnesium chloride (Anhydrous) | 95.21 | 2.26E+04 | 2.37E-01 |
| Magnesium Sulfate ($MgSO_4$) | 120.37 | 3.84E+04 | 3.19E-01 |
| Potassium chloride (KCl) | 74.55 | 2.43E+05 | 3.26E+00 |
| Sodium bicarbonate ($NaHCO_3$) | 84.01 | 1.51E+06 | 1.80E+01 |
| Sodium chloride (NaCl) | 58.44 | 5.53E+06 | 9.46E+01 |
| Sodium phosphate, dibasic (Anhydrous) | 141.96 | 5.56E+04 | 3.92E-01 |
| Sodium phosphate, monobasic monohydrate ($NaH_2PO_4$—$H_2O$) | 137.99 | 4.90E+04 | 3.55E-01 |
| TRACE MINERALS | | | |
| Ferric Nitrate ($Fe(NO_3)_3$—$9H_2O$) | 404 | 3.92E+01 | 9.71E-05 |
| Ferrous sulfate heptahydrate ($FeSO_4$—$7H_2O$) | 278.01 | 3.28E+02 | 1.18E-03 |
| Copper(II) sulfate pentahydrate ($CuSO_4$—$5H_2O$) | 249.69 | 1.02E+00 | 4.08E-06 |
| Zinc sulfate heptahydrate ($ZnSO_4$—$7H_2O$) | 287.56 | 3.39E+02 | 1.18E-03 |
| Ammonium Metavanadate $NH_4VO_3$ | 116.98 | 1.28E+00 | 1.09E-05 |
| Manganese Sulfate monohydrate ($MnSO_4$—$H_2O$) | 169.02 | 3.33E-01 | 1.97E-06 |
| $NiSO_4$—$6H_2O$ | 262.85 | 2.55E-01 | 9.70E-07 |
| Selenium | 78.96 | 1.40E+01 | 1.77E-04 |
| Sodium Meta Silicate $Na_2SiO_3$ $9H_2O$ | 284.2 | 2.75E+02 | 9.66E-04 |
| $SnCl_2$ | 189.62 | 2.35E-01 | 1.24E-06 |
| Molybdic Acid, Ammonium salt | 1235.86 | 2.43E+00 | 1.97E-06 |
| $CdCl_2$ | 183.32 | 2.24E+00 | 1.22E-05 |
| $CrCl_3$ | 158.36 | 3.14E-01 | 1.98E-06 |
| $AgNO_3$ | 169.87 | 1.67E-01 | 9.81E-07 |
| $AlCl_3$ $6H_2O$ | 241.43 | 1.18E+00 | 4.87E-06 |
| Barium Acetate ($Ba(C_2H_3O_2)_2$) | 255.42 | 2.50E+00 | 9.79E-06 |
| $CoCl_2$ $6H_2O$ | 237.93 | 2.33E+00 | 9.81E-06 |
| $GeO_2$ | 104.64 | 5.20E-01 | 4.97E-06 |
| KBr | 119 | 1.18E-01 | 9.89E-07 |
| KI | 166 | 1.66E-01 | 1.00E-06 |
| NaF | 41.99 | 4.13E+00 | 9.83E-05 |

TABLE 5-continued mTeSR1 formulation.

| mTeSR1 Ingredient | molar mass (g/mol) | Concentration (ng/mL) | Concentration (mM) |
|---|---|---|---|
| RbCl | 120.92 | 1.19E+00 | 9.81E−06 |
| ZrOCl$_2$ 8H$_2$O | 178.13 | 1.75E+00 | 9.80E−06 |
| ENERGY SUBSTRATES | | | |
| D-Glucose | 180.16 | 2.47E+06 | 1.37E+01 |
| Sodium Pyruvate | 110.04 | 4.31E+04 | 3.92E−01 |
| LIPIDS | | | |
| Linoleic Acid | 280.45 | 5.27E+01 | 1.88E−04 |
| Lipoic Acid | 206.33 | 8.25E+01 | 4.00E−04 |
| Arachidonic Acid | 304.47 | 3.93E+00 | 1.29E−05 |
| Cholesterol | 386.65 | 4.33E+02 | 1.12E−03 |
| DL-alpha tocopherol-acetate | 472.74 | 1.37E+02 | 2.90E−04 |
| Linolenic Acid | 278.43 | 1.95E+01 | 6.99E−05 |
| Myristic Acid | 228.37 | 1.96E+01 | 8.59E−05 |
| Oleic Acid | 282.46 | 1.96E+01 | 6.94E−05 |
| Palmitic Acid | 256.42 | 1.96E+01 | 7.65E−05 |
| Palmitoleic acid | 254.408 | 1.96E+01 | 7.71E−05 |
| Stearic Acid | 284.48 | 1.96E+01 | 6.89E−05 |
| AMINO ACIDS | | | |
| L-Alanine | 89.09 | 1.22E+04 | 1.37E−01 |
| L-Arginine hydrochloride | 147.2 | 8.07E+04 | 5.48E−01 |
| L-Asparagine-H$_2$O | 150.13 | 2.06E+04 | 1.37E−01 |
| L-Aspartic acid | 133.1 | 1.82E+04 | 1.37E−01 |
| L-Cysteine-HCl—H$_2$O | 175.63 | 1.38E+04 | 7.83E−02 |
| L-Cystine dihydrochloride | 313.22 | 2.45E+04 | 7.83E−02 |
| L-Glutamic acid | 147.13 | 2.02E+04 | 1.37E−01 |
| L-Glutamine | 146.15 | 4.30E+05 | 2.94E+00 |
| Glycine | 75.07 | 2.21E+04 | 2.94E−01 |
| L-Histidine monohydrochloride monohydrate | 209.63 | 2.47E+04 | 1.18E−01 |
| L-Isoleucine | 131.17 | 4.28E+04 | 3.26E−01 |
| L-Leucine | 131.17 | 4.64E+04 | 3.54E−01 |
| L-Lysine hydrochloride | 182.65 | 7.14E+04 | 3.91E−01 |
| L-Methionine | 149.21 | 1.35E+04 | 9.06E−02 |
| L-Phenylalanine | 165.19 | 2.79E+04 | 1.69E−01 |
| L-Proline | 115.13 | 2.49E+04 | 2.16E−01 |
| L-Serine | 105.09 | 3.09E+04 | 2.94E−01 |
| L-Threonine | 119.12 | 4.19E+04 | 3.52E−01 |
| L-Tryptophan | 204.23 | 7.07E+03 | 3.46E−02 |
| L-Tyrosine disodium salt hydrate | 225.15 | 3.78E+04 | 1.68E−01 |
| L-Valine | 117.15 | 4.16E+04 | 3.55E−01 |
| VITAMINS | | | |
| Ascorbic acid | 176.12 | 4.46E+04 | 2.53E−01 |
| Biotin | 244.31 | 2.74E+00 | 1.12E−05 |
| B12 | 1355.37 | 5.34E+02 | 3.94E−04 |
| Choline chloride | 139.62 | 7.02E+03 | 5.03E−02 |
| D-Calcium pantothenate | 238.27 | 8.79E+02 | 3.69E−03 |
| Folic acid | 441.4 | 2.08E+03 | 4.71E−03 |
| i-Inositol | 180.16 | 9.89E+03 | 5.49E−02 |
| Niacinamide | 122.12 | 1.59E+03 | 1.30E−02 |
| Pyridoxine hydrochloride | 205.64 | 1.57E+03 | 7.62E−03 |
| Riboflavin | 376.36 | 1.72E+02 | 4.56E−04 |
| Thiamine hydrochloride | 337.27 | 8.16E+03 | 2.42E−02 |
| GROWTH FACTORS/PROTEINS | | | |
| GABA | 103.12 | 1.01E+05 | 9.79E−01 |
| Pipecolic Acid | 129 | 1.27E+02 | 9.84E−04 |
| bFGF | 18000 | 1.04E+02 | 5.77E−06 |
| TGF beta 1 | 25000 | 5.88E−01 | 2.35E−08 |
| Human Insulin | 5808 | 2.28E+04 | 3.92E−03 |
| Human Holo-Transferrin | 78500 | 1.08E+04 | 1.37E−04 |
| Human Serum Albumin | 67000 | 1.31E+07 | 1.95E−01 |
| Glutathione (reduced) | 307.32 | 1.96E+03 | 6.38E−03 |
| OTHER COMPONENTS | | | |
| Hypoxanthine Na | 136.11 | 1.61E+03 | 1.18E−02 |
| Phenol red | 354.38 | 5.99E+03 | 1.69E−02 |
| Putrescine-2HCl | 161.07 | 6.36E+01 | 3.95E−04 |
| Thymidine | 242.229 | 2.86E+02 | 1.18E−03 |
| 2-mercaptoethanol | 78.13 | 7.66E+03 | 9.80E−02 |

TABLE 5-continued mTeSR1 formulation.

| mTeSR1 Ingredient | molar mass (g/mol) | Concentration (ng/mL) | Concentration (mM) |
|---|---|---|---|
| Pluronic F-68 | 8400 | 1.96E+05 | 2.33E−02 |
| Tween 80 | 1310 | 4.31E+02 | 3.29E−04 |

The systems containing a LN-521/e-cadherin substrate and mTeSR1 medium with additional albumin work extremely well for maintaining and proliferating undifferentiated stem cells (e.g. embryonic and induced pluripotent stem cells) in a completely chemically defined environment and xeno-free conditions without feeders or any inhibitors of apoptosis.

In this context, LN-521 and LN-511 can be used in a substrate combined with e-cadherin. The LN-521/LN-511 may be present as an intact protein or as a protein fragment. Again, a "fragment" contains one, two, or three functional domains that possesses binding activity to another molecule or receptor. Generally, any effective laminin may be used, wherein the effectiveness is determined by whether stem cells can proliferate upon the substrate. The laminins are usually recombinant as well.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method for maintaining stem cells, comprising:
   plating the stem cells on a substrate comprising a laminin and a cadherin,
   wherein the laminin is an intact protein; and
   exposing the stem cells to a cell culture medium comprising at least 0.3 mM of albumin;
   wherein the laminin is laminin-521;
   wherein the cadherin is e-cadherin; and
   wherein the weight ratio of the laminin-521 to the e-cadherin is from 5:1 to 10:1.

2. The method of claim 1, wherein the cell culture medium is mTeSR1 medium with additional albumin to arrive at an albumin concentration of at least 0.3 mM.

3. The method of claim 1, wherein the substrate and the medium do not contain any differentiation inhibitors, feeder cells, differentiation inductors, or apoptosis inhibitors.

4. The method of claim 1, wherein the stem cells are plated at a density of 200 cells/mm$^2$ or less.

5. The method of claim 1, wherein the stem cells are plated at a density of 200 cells/mm$^2$ or more.

6. The method of claim 1, wherein the stem cells are plated such that no two stem cells contact each other.

7. The method of claim 1, wherein the cell culture medium is mTeSR1 medium with about 0.39 mM albumin.

8. The method of claim 1, wherein the albumin is human serum albumin.

9. The method of claim 1, wherein the human serum albumin is recombinant human serum albumin.

10. The method of claim 1, wherein the laminin is an effective recombinant laminin.

* * * * *